US009149569B2

(12) United States Patent
Hariri

(10) Patent No.: US 9,149,569 B2
(45) Date of Patent: *Oct. 6, 2015

(54) TREATMENT OF DISEASES OR DISORDERS USING PLACENTAL STEM CELLS

(75) Inventor: Robert J. Hariri, Florham Park, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/108,871

(22) Filed: May 16, 2011

(65) Prior Publication Data

US 2011/0217271 A1 Sep. 8, 2011

Related U.S. Application Data

(63) Continuation of application No. 12/341,961, filed on Dec. 22, 2008, now Pat. No. 7,976,836, and a continuation of application No. 12/259,259, filed on Oct. 27, 2008, which is a continuation of application No. 10/874,828, filed on Jun. 22, 2004, now Pat. No. 7,468,276, which is a continuation of application No. 10/076,180, filed on Feb. 13, 2002, now abandoned, application No. 13/108,871, which is a continuation-in-part of application No. 10/004,942, filed on Dec. 5, 2001, now Pat. No. 7,045,148.

(60) Provisional application No. 60/268,560, filed on Feb. 14, 2001, provisional application No. 60/251,900, filed on Dec. 6, 2000.

(51) Int. Cl.

| C12N 5/071 | (2010.01) |
|---|---|
| A61M 1/02 | (2006.01) |
| C12N 5/073 | (2010.01) |
| C12N 5/0775 | (2010.01) |
| A61K 35/12 | (2015.01) |
| A61K 48/00 | (2006.01) |

(52) U.S. Cl.
CPC .............. *A61M 1/02* (2013.01); *C12N 5/0603* (2013.01); *C12N 5/0605* (2013.01); *C12N 5/0668* (2013.01); *A61K 35/12* (2013.01); *A61K 48/00* (2013.01); *A61M 2202/0462* (2013.01); *A61M 2210/1458* (2013.01); *A61M 2210/1466* (2013.01); *C12N 2509/00* (2013.01); *C12N 2510/02* (2013.01); *C12N 2533/90* (2013.01)

(58) Field of Classification Search
None
See application file for complete search history.

(56) References Cited

U.S. PATENT DOCUMENTS

| 3,862,002 A | 1/1975 | Sanders |
|---|---|---|
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,356,373 A | 10/1994 | Dracker et al. |
| 5,372,581 A | 12/1994 | Anderson |
| 5,415,665 A | 5/1995 | Hessel et al. |
| 5,437,994 A | 8/1995 | Emerson et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |

(Continued)

FOREIGN PATENT DOCUMENTS

| CN | 1548529 | 5/2003 |
|---|---|---|
| EP | 0333328 | 9/1989 |

(Continued)

OTHER PUBLICATIONS

Malliaras et al. Clin Pharmacol Ther Oct. 2011;90:532-40.*
Barry, "Where do all the placentas go?" Canadian Journal of Infection Control 9(1):8-10 (1994).
Chen, et al. "Intravaneous Administration of Human Umbilical Cord Reduces Behavioral Deficits after Stroke in Rats," Stroke 32(11): 2682-2688 (2001).
Conget et al., "Phenotypical and functional properties of human bone marrow mesenchymal progenitor cells" Journal of Cellular Physiology 181:67-73 (1999).
U.S. Appl. No. 13/071,437, filed Mar. 24, 2011, Zhang et al.
U.S. Appl. No. 13/089,029, filed Apr. 18, 2011, Hariri et al.
U.S. Appl. No. 13/107,727, filed May 13, 2011, Edinger et al.
U.S. Appl. No. 13/107,778, filed May 13, 2011, Edinger et al.
U.S. Appl. No. 13/108,891, filed May 16, 2011, Hariri.
U.S. Appl. No. 13/108,901, filed May 16, 2011, Hariri.
U.S. Appl. No. 13/182,250, filed Jul. 13, 2011, Hariri et al.

(Continued)

*Primary Examiner* — Janice Li
(74) *Attorney, Agent, or Firm* — Jones Day

(57) ABSTRACT

The present invention provides a method of extracting and recovering embryonic-like stem cells, including, but not limited to pluripotent or multipotent stem cells, from an exsanguinated human placenta. A placenta is treated to remove residual umbilical cord blood by perfusing an exsanguinated placenta, preferably with an anticoagulant solution, to flush out residual cells. The residual cells and perfusion liquid from the exsanguinated placenta are collected, and the embryonic-like stem cells are separated from the residual cells and perfusion liquid. The invention also provides a method of utilizing the isolated and perfused placenta as a bioreactor in which to propagate endogenous cells, including, but not limited to, embryonic-like stem cells. The invention also provides methods for propagation of exogenous cells in a placental bioreactor and collecting the propagated exogenous cells and bioactive molecules therefrom.

10 Claims, 8 Drawing Sheets

(56) References Cited

U.S. PATENT DOCUMENTS

| | | |
|---|---|---|
| 5,670,351 A | 9/1997 | Emerson et al. |
| 5,672,346 A | 9/1997 | Srour et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,497,875 B1 | 12/2002 | Sorrell et al. |
| 6,528,245 B2 | 3/2003 | Sanchez-Ramos et al. |
| 6,541,024 B1 | 4/2003 | Kadiyala et al. |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 7,029,666 B2 | 4/2006 | Bruder et al. |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,875,272 B2 | 1/2011 | Messina et al. |
| 7,875,273 B2 | 1/2011 | Messina et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 2001/0005591 A1 | 6/2001 | Qasba et al. |
| 2002/0102239 A1 | 8/2002 | Koopmans |
| 2002/0123141 A1 | 9/2002 | Hariri |
| 2002/0132343 A1 | 9/2002 | Lum |
| 2002/0160510 A1 | 10/2002 | Hariri |
| 2003/0032179 A1 | 2/2003 | Hariri |
| 2003/0044977 A1 | 3/2003 | Sakuragawa et al. |
| 2003/0180269 A1 | 9/2003 | Hariri |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |

(56) References Cited

U.S. PATENT DOCUMENTS

| | | |
|---|---|---|
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0126482 A1 | 5/2009 | Heidaran et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |

FOREIGN PATENT DOCUMENTS

| | | |
|---|---|---|
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 98/37903 | 9/1998 |
| WO | WO 99/64566 | 12/1999 |
| WO | WO 00/17325 | 3/2000 |
| WO | WO 00/27999 | 5/2000 |
| WO | WO 00/69335 | 11/2000 |
| WO | WO 00/73421 | 12/2000 |
| WO | WO 01/21767 | 3/2001 |
| WO | WO 01/93909 | 12/2001 |
| WO | WO 02/46373 | 6/2002 |
| WO | WO 02/064755 | 8/2002 |
| WO | WO 03/042405 | 5/2003 |
| WO | WO 03/068937 | 8/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/047770 | 6/2004 |
| WO | WO 2004/071283 | 8/2004 |
| WO | WO 2005/042703 | 5/2005 |
| WO | WO 2005/097190 | 10/2005 |
| WO | WO 2005/105992 | 11/2005 |
| WO | WO 2006/015214 | 2/2006 |
| WO | WO 2007/047465 | 4/2007 |
| WO | WO 2007/047468 | 4/2007 |
| WO | WO 2007/079183 | 7/2007 |
| WO | WO 2008/019148 | 2/2008 |
| WO | WO 2008/051568 | 5/2008 |
| WO | WO 02/063962 | 8/2008 |
| WO | WO 2008/010497 | 8/2008 |

OTHER PUBLICATIONS

Denison et al., "Cytokine secretion by human fetal membranes, decidua and placenta at term" Human Reproduction 13(12):3560-3565 (1998).

Extended European Search Report dated Mar. 11, 2011 for EP Application No. 10183435.6-2401 (specification corresponding to U.S. Patent No. 7,045,148).

Extended European Search Report dated Mar. 22, 2011 for EP Application No. 10183252.5-2401 (specification corresponding to U.S. Patent No. 7,311,904).

Extended European Search Report dated Mar. 25, 2011 for EP Application No. 10182105.7-2401 (specification corresponding to U.S. Patent No. 7,468,276).

Extended European Search Report dated Mar. 25, 2011 for EP Application No. 10182243.5-2401 (specification corresponding to U.S. Patent No. 7,468,276).

Extended European Search Report dated Mar. 25, 2011 for EP Application No. 10182362.3-2401 (specification corresponding to U.S. Patent No. 7,468,276).

(56) References Cited

OTHER PUBLICATIONS

Extended European Search Report dated Mar. 25, 2011 for EP Application No. 10182485.2-2401 (specification corresponding to U.S. Patent No. 7,468,276).
Extended European Search Report dated Mar. 25, 2011 for EP Application No. 10183301.0-2401 (specification corresponding to U.S. Patent No. 7,311,904).
Extended European Search Report dated Mar. 28, 2011 for EP Application No. 10182433.2-2401 (specification corresponding to U.S. Patent No. 7,468,276).
Extended European Search Report dated Mar. 3, 2011 for EP Application No. 10183378.8-2401 (specification corresponding to U.S. Patent No. 7,045,148).
Extended European Search Report dated Mar. 30, 2011 for EP Application No. 10182303.7-2401 (specification corresponding to U.S. Patent No. 7,468,276).
Extended European Search Report for EP Application No. 10184356.3-1222 (specification corresponding to U.S. Patent No. 7,311,905).
Extended European Search Report for EP Application No. 10185142.6-1222 (specification corresponding to U.S. Patent No. 7,311,905).
Hsieh et al., "Effects of glucose on placental hormones in the human term placenta in vitro" J. Formos, Med. Assoc. 96:309-313 (1997).
Jaroscak et al., "Preliminary characterization of the surface staining of placental derived adherent cells: a potential new source of stroma for umbilical cord blood (UCB) expansion," Blood 96(11, Pt 2) (2000).
Nagayma et al., "Immunological reconstitution after cord blood transplantation for an adult patient", Bone Marrow Transplantation 24: 211-13 (1999).
Parolini, et al., "Concise Review: Isolation and Characterization of Cells from Human Term Placenta: Outcome of the First International Workshop on Placenta Derived Stem Cells." Stem Cells 26:300-311 (2008).
Ponticiello et al., "Gelatin-based resorbable sponge as a carrier matrix for human mesenchymal stem cells in cartilage regeneration therapy" Journal of Biomedical Materials Research 52:246-255 (2000).
Yen et al, "Isolation of multipotent cells from human term placenta" Stem Cells (Dayton, Ohio) 2005, vol. 23, No. 1, pp. 3-9, XP002443187 ISSN: 1065-5099 (Jan. 2005).
Yin et al., "AC133, a novel marker for human hematopoietic stem and progenitor cells" Blood 90(12):5002-5012 (1997).
Non-Final Office Action dated Apr. 21, 2011 in U.S. Appl. No. 11/648,804.
Non Final Office Action dated Apr. 18, 2011 in U.S. Appl. No. 12/030,170.
U.S. Appl. No. 13/081,415, filed Apr. 6, 2011, Abbot.
U.S. Appl. No. 13/081,422, filed Apr. 6, 2011, Edinger.
Abott, "ABCG2 (BCRP) Expression in Normal and Malignant Hematopoietic Cells," Hematol. Oncol. 21:115-130 (2003).
Abe, "Threapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).
Abkowtiz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Aplin, "Implantation, trophoblast Differentiation and Haemochorial Placentation: Mechanistic Evidence in vivo and in vitro," Journal of Cell Science 99:681-692 (1991).
Ballin, et al., "Autologous Umbilical Cord Blood Transfusion," Arch. Dis. Child Fetal Neonatal. Ed. 73(3):F181-F183 (1995).
Barlow et al., "Comparison of Human Placenta- and Bone Marrow-Derived Multipotent Mesenchymal Stem Cells," Stem Cells and Development 17:1095-1108 (2008).
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(−) Progenitor Cell Recovery Using a Novel Umbilical Cord Blood Collection System," Stem Cells 18(4):245-251 (2000).
Bertolini, et al., "Retrovirus-Mediated Transfer of the Multidrug Resistance Gene into Human Haemopoietic Progenitor Cells," Haemolotol. 68:318-324 (1994).
Bloxam et al., "Culture of Syncytiotrophoblast For The Study of Human Placental Transfer. Part I: Isolation and Purification of Cytotrophoblast," Placenta 18:93-98 (1997).
Bloxam, "Human Placental Trophoblast Culture: One-Sided and Two-Sided Models," Proceedings of the Nutrition Society 50:349-354 (1991).
Bullen et al., "Two-Sided Culture of Human Placental Trophoblast. Morphology, Immunocytochemistry and Permeability Properties," Placenta 11:431-450 (1990).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Cester et al., "Cation Transport Across Cultured Trophoblast Membrane in Preeclampsia," Clin. and Exper. Hyper. in Pregnancy, B11(1):59-69 (1992).
Chies et al., "Sickle Cell Disease: A Chronic Inflammatory Condition," Medical Hypotheses 57(1):46-50 (2001).
Contractor, et al., "A comparison of the effects of different perfusion regimens on the structure of the isolated human placental lobule," Cell Tissue Res. 237:609-617 (1984).
Cord Blood Stem Cell, Mesh Term Database 2003.
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Deans et al., Exp. Hematol. 28: 875-84 (2000).
Dorrel "Expansion of Human Cord Blood CD34+CD38− Cells in ex vivo Culture during Retroviral Transduction without a Corresponding Increase in SCID Repopulation cell (SRC) Frequency: Dissociation of SRC Phenotype and Function," Blood 95(1):102-110 (2000).
Dushnik-Levinson, et al. "Embryogenesis in vitro: study of differentiation of embryonic stem cells." Biol Neonate. 67(2):77-83 (1995).
Elchalal, et al., "Postpartum Umbilical Cord Blood Collection for Transplantation: a Comparison of Three Methods," Am. J. of Obstetrics & Gyn. 182(1 Pt 1):227-232 (2000).
Emerson, et al., "Ex vivo Expansion of Hematopoietic Precursors, Progenitors and Stem Cells: the Next Generation of Cellular Therapeutics," Blood 87(8):3082-3088 (1996).
Ende, et al., "Pooled Umbilical Cord Blood as a Possible Universal Donor for Marrow Reconstitution and Use in Nuclear Accidents," Life Sci. 69:1531-1539 (2001).
Erices, et al., "Mesenchymal Progenitor Cells in Human Umbilical Cord Blood," Br. J. Haemotol. 109(1):235-242 Abstract (2000).
Fasouliotis, et al., "Human umbilical cord blood banking and transplantation: a state of the art," Eur. J. Obstet. Gynecol. Reprod. Biol. 90(1):13-25 (2000).
Fassas, et al., "Autologous Stem Cell Transplantation in Progressive Multiple Sclerosis—An Interim Analysis of Efficacy," J. Clin. Immunol., 20(1)24-30 (2000).
Fisher et al., "Adhesive and Degradatie Properties of Human Placental Cytotrophoblast Cells In Vitro," Journal od Cell Biology 109:891-902 (1989).
Frank H G, et al., "Cell culture models of human trophoblast: primary culture of trophoblast—a workshop report." Placent Apr. 2001, vol. 22 Suppl A. pp. S107-S109, XP002443188 ISSN: 0143-4004 (Apr. 2001).
Genbacev et al., "Regulation of Human Placental Development by Oxygen Tension," 277(5332):1669-1672 (1997).

(56) References Cited

OTHER PUBLICATIONS

Greenwood et al., "Membrane Potential Difference and Intracellular Cation Concentrations in Human Placental Trophoblast Cells in Culture," Journal of Physiology 492.3:629-640 (1996).
Harun et al., "Cytotrophoblast Stem Cell Lines Derived from Human Embyonic Stem Calls and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeotidase/Oxytocinase," J. Biochem. 125(5):931-938 (1999).
Hatzopoulos, et al., "Isolation and characterization of endothelial progenitor cells from mouse embryos," Deveiopment. 125(8):1457-68 (1998).
Heidaran, Disclosure Document No. 457045 for "A Method of Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Himori, et al., Chemotherapeutic susceptibility of human bone marrow progenitor cells and human myelogenous leukemia cells (HL-60) in co-culture; preliminary report. Int J Cell Cloning. 2(4):254-62 (1984).
Hirano et al., "CD9 is Expressied in Extravillous Trophoblasts in Association with Integrin α3 and integrin α5," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hume et al., "Red Blood Cell Transfusions For Preterm Infans: The Role of Evidence-Based Medicine," Seminars in Perinatology, W.B. Saunders, GB 21(1):14-15 (1997).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
James et al., "Cytotrophobast Differentiation In The First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcripition Factor Mash-2 (Mammalian Achaete-Scute Homologous Protein-20," Molecular Endocrinology 14(10):1661-1673 (2000).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in The Human Placenta," Trophoblast Research 10:21-65 (1997).
Kavalerchik E et al. "Chronic myeloid leukemia stem cells," J Clin Oncol 26:2911-2915(2008).
Kawata, et al., "Transcriptional Control of HLA-A,B,C Antigen in Human Placental Cytotrophoblast Isolated Using Trophoblast- and HLA-Specific Monoclonal Antibodies and the Fluorescence-Acivated Cell Sorter," J. Exp. Med. 160(3):633-51 (1984).
Kliman et al., "Purification, Characterization, and In Vitro Differentiation of Cytotrophoblasts from Human Term Placentae," Endocrinology 118(4):1567-1582 (1986).
Korbling, et al., "Hepatocytes and Epithelial Cells of Donor Origin in Recipients of Peripheral-Blood Stem Cells," N. Engl. J. Med. 346(10):738-746 (2002).

Kurtzberg, "Placental Blood as a Source of Hmatopoietic Sem Cells for Transplantation into Unrelated Recipients," N. Engl. J. Med. 355:157-166 (1996).
Landon et al., "The Effects of Ethanol Methotrexate and Diphenylhydantoin on [$^{14}$C] Leucine Incorporation by Human Trophoblasst Cells Cultured In Vitro," British Journal of Obstetrics and Gynaecology 94:252-255 (1987).
Larsson, et al., "Serum and Plasma Levels of FGF-2 and VEGF in Healthy Blood Donors," Angiogenesis 5:107-110 (2002).
Leonard, et al., "The Role of ABC Transporters in Clinical Practice," Oncologist. 8:411-424 (2003).
Lipinski et al., "Human Trophoblast Cell-Surface Antigen Defined by Monoclonal Antibodies," Proc. Natl. Acad. Sci. USA, Medical Sciences 78(8);5147-5150 (1981).
Loke et al., "Identification of Cytotrophoblast Colonies in Cultures of Human Placental Cells Using Monoclonal Antibodies," Placenta 7:221-231 (1986).
Lowy, et al., "Isolation of transforming DNA; cloning the hamster aprt gene," Cell. 22(3);817-23 (1980).
Ma, et al., "Development of an in vitro Human Placenta Model by the Cultivation of Human Trophoblasts in a Fiber-Based Bioreactor System," Tissue Engineering 5, 91-102. (1999).
MacLaren, et al., 1992, Inter- and Intraspecific Palcentae in Sheep, Goats and Sheep-Goat Chimaeras, J Comp Pathol, 106:279-297.
Madri et al., "Capillary Endothelial Cell Cultures: Phenotypic Modulation by Matrix Components," J. Cell Biol. 97:153-165 (1983).
Marmont, "New Horizons in the Treatment if Autoimmune Diseases: Immunoablation and Stem Cell Transplantation," Ann. Rev. Medicine 51:115-134 (2000).
Melchner, et al., "Human Placental Conditioned Medium Reverses Apparent Commitment to Differentiation of Human Promyelocytic Leukemia Calls (HL60)," Blood 66(6):1469-1472 (1985).
Minguell, et al., "Mesenchymal Stem Cells," Exp. Biol. Med. 226:507-520 (2001).
Moore, et al., "A Simple Perfusion Technique for Isolation of Maternal Intervillous Blood Mononuclear Cells from Human Placentae," J. Immunol. Methods 209(1):93-104 (1997).
Morgan et al., "Human Placental Cell Culture," Biochemical Society Transactions 12 (1984).
Morgan et al., "Long-Term Culture of Human Trophoblast Cells," British Journal of Obstetrics and Gynaecology 92:84-92 (1985).
Morrish et al., "Epidermal Growth Factor Induces Differentiation and Secretion of Human Chorionic Gonadotropin and Placental Lactogen in Normai Human Placenta," Journal of Clinical Endocrinology and Metabolism 65(6):1282-1290 (1987).
Morrish et al., "In Vitro Cultured Human Term Cytotrophoblast; A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 18:387-373 (1995).
Myllynen "In Search of Models for Hepatic and Placental Pharmacokinetics," [Dissertation] University of Oulu, (2003).
Nadkarni, et al., "Effect of Retinoic Acid on Bone-Marrow Committed Stem Cells (CFU-c) from Chronic myeloid Leukemia Patients," Tumori. 70(6):503-505 (1984).
Oda et al., "Trophoblast Stem Cells," Methods in Enxymology 419(15):387-400 (2006).
Oppenheim, et al., 2001, Evidence against humoral immune attach as the cause of sheep-goat interspecies and hybrid pregnancy failure in the doe, Theriogenology 55:1567-1581.
Ordi, et al., "Massive Chronic Intervilllositis of the Placenta Associated with Malaria Infection," Am. J. Surg. Pathol. 8:1006-1011 (1998).
Pande et al., "Isolation and Culture of Hamster Ectoplacental Cone Trophoblasts: an In Vitro Study on the Cell Types and Their Growth Pattern," Cell Prolif, 29:163-171 (1996).
Papaioannou, et al., "Stem Cells from Early Marnrnalien Embryos" Stem Cells Handbook:19-31 (2004).
Petroff et al., "Isolation and Culture of Term Human Trophoblast Cells," Methods in Molecular Medicine, Placenta and Trophoblast, 1(16):203-217 (2006).

(56) References Cited

OTHER PUBLICATIONS

Pittenger., et al., "Multilineage Potential of Adult Human Mesenchymal Stem Cells," Science 284(5411):143-147 (1999).

Potgens et al., "Human Trophoblast Contains an Intracellular Protein Reactive with and Antibody against CD133—A Novel Marker for Trophoblast," Placenta 22:639-645 (2001).

Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).

Quinn et al., "Mouse Trophoblast Stem Cells," Methods in Molecular Medicine 121(1)125-148 (2005).

Rachmilewitz et al., "Intermediate Cells During Cytotrphoblast Differentiation in Vitro," Cell Growth & Differentiation 4:395-402 (1993).

Reubinoff, "Neural Progenitors from Human Embryonic Stem Cells," Nature Biotech. 19(12):1134-1140 (2001).

Reyes, et al., "Purification and ex vivo Expansion of Postnatal Human Marrow Mesodermanl Progenitor Cells," Blood 98(9):2615-2625 (2001).

Reyes, et al., Origin of endothelial progenitors in human postnatal bone marrow.J Clin Invest. 109(3):337-46 (2002).

Rielland et al., "Trophoblast Stem Cell Derivation, Cross-species Comparison and Use of Nuclear Transfer: New Tools to Study Trophoblast Growth and Differentiation," Developmental Biology 322:1-10 (2008).

Ringler et al., "In Vitro Systems for the Study of Human Placental Endocrine Function," Endocrine Reviews 11(1):105-123, 1990.

Rong-Hao et al., "Establishment and Characterization of a Cytotrophoblast Cell Line From Normal Placenta of Human Origin," Human Reproduction 11(6):1328-1333 (1996).

Sapin, "Esterification of Vitamin A by the Human Placenta Involves Villous Mesenchymal Fibrlboasts," pediatric Research 48(4):565-572 (2000).

Saric et al., "An IFN-γ-induced Aminopeptidase in the ER, ERAP I, Trims Precursors to MHC Class I-presented Peptides," Nature Immunology 3(12):1169-1176 (2002).

Schulz et al., "Human Embryonic Stem Cells as Models For Trophoblast Differentiation," Placenta 29(Suppl A):S10-S16 (2008).

Schwab, "Fast and Reliabie Culture Method for Cells from 8-10 Week Trophoblast Tissue," Lancet 323:1082 (1984).

Shamblott, et al., "Derivation of Pluripotent Stem Cells from Cultured Human Primordial Germ Celis," Proc. Natl. Acad. Sci. USA 95(23):13726-13731 (1998).

Sikkema-Raddatz, "Four Years' Cytogenetic Experience with the Culture of Chorionic Villi," Prenatal Diagnosis 20:950-955 (2000).

Slager, Transforming growth factor-beta in the early mouse embryo: implications for the regulation of muscle formation and implantation. Dev Genet. 14(3):212-24 (1993).

Soma, "Human Trophoblast in Tissue Culture," Obstetrics and Gynaecology 18(6):704-718 (1961).

Srour, "Ex vivo Expansion of Hematopoiectic Stem and Progenitor Cells. Are We There Yet?" J. Hematother. 8:93-102 (1999).

Stromberg et al., "Isolation of Functional Human Trophoblast Cells and Their Partial Characterization Primary Cell Culture," In Vitro 14(7):6331-638 (1978).

Stromberg et al., "Methods in Cell Biology, Chapter 10: The Human Placenta in Cell and Organ Culture," 21:227-252 (1980).

Sunderland et al., "HLA A, B, C Antigens Are Expressed on Nonvillous Trophoblast of the Early Human Placenta," Journal of Immunology 127(6):2614-2615 (1981).

Tarrade et al., "Characterization of Human Villous and Extrovilious Trophoblasts Isolated from First Trimester Placenta," Laboratory Investigation 81(9):1199-1211 (2001).

Thomson, et al., Embryonic stem cell lines derived from human blastocysts. Science. 282 (5391): 1145-7 (1998).

Truman et al., "Human Placental Cytotrophoblast Cells: Identification and Culture," Arch Gynecol. Obstet. 246:39-49 (1989).

Truman et al., "The Effects of Substrate and Epidermal Growth Factor on Human Placental Trophoblast Cells in Culture," In Vitro Cellular & Developmental Biology 22(9):525-528 (1986).

Turner, et al., "A modified Harvest Technique for Cord Blood Hematopoietic Stem Cells," Bone Marrow Transolantation 10:89-91 (1992).

Van Bekkum, "The Pluripotent Hemopoietic Stem Cell: It's Identification and Applications," Verh. Dtsch. Ges. Patol. 74:19-24 (1990).

Vawda et al., "Stem Cell Therapies for Perinatal Brain Injuries", Seminars in Fetal and Neonatal Medicine, Elsevier, GB 12(4):259-272 (2007).

Viacord, Umblicical cord blood can save lives (Informational brochure), Boston: ViaCell CENTR-BRO R1 10/01 (2001).

Wang, et al., "Enhanced Recovery of Hematopoietic Progenitor and Stem Cells from Cultivated, Postpartum Human Placenta," Blood 98(11/1):183a Abstract No. 769 (2001).

Woods, et al., "Osomometric and permeability characteristics of human placental/umbilical cord blood CD34+ cells and their application to cryopreservation," J. Hematother. Stem Cell Res. 9(2):161-173 (2000).

Xu et al., "BMP4 Initiates Human Embryonic Stem Cell Differentiation to Trophoblast," Nature Biology, 20:1261-1264 (2002).

Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).

Yan, et al., Retinoic acid promotes differentiation of trophoblast stem cells to a giant cell fate. Dev Biol. 235(2):422-32 (2001).

Ye, et al., "Recovery of Placental-Derived Adherent Cells with Mesenchymal Stem Cell Characteristics," Blood 98(11/1):147b Abstract No. 4260 (2001).

Yeger et al., "Enzymatic Isolation of Human Trophoblast and Culture on Various Substrates: Comparison of First Trimester with Term Trophoblast," Placenta 10:137-151 (1989).

Yui et al., "Functional, Long-term Cultures of Human Term Trophoblasts Purified by Column-elimination of CD9 Expressing Cells," Placenta 15:231-246 (1994).

Zhao, et al., "Transplanted Human Bone Marrow-Derived Adult Stem Cells Survive and Improve Functional Outcome in a Rat Model of Cortical Ischemic Brain Injury," Experimental Neurology, Academic Press, New York, 164(2):465-466, XP001159669 (2000).

Zhao, et al., "Human Bone Marrow Stem Cells Exhibit Neural Phenotypes After Transplantation and Ameliorate Neurological Deficits with Ischemic Brain Injury Rats," Abstract of the Annual Meeting of the Society for Neuroscience, Society ot Neruoscience, Washington DC, 26(1/02): 860.01 XP001159670 (2000).

Advisory Action dated Jul. 12, 2004 in U.S. Appl. No. 10/076,180.

Office Action dated Aug. 28, 2003 in U.S. Appl. No. 10/076,180.

Office Action dated Jun. 20, 2005 in U.S. Appl. No. 10/076,180.

Office Action dated Mar. 18, 2004 in U.S. Appl. No. 10/076,180.

Office Action dated Oct. 20, 2004 in U.S. Appl. No. 10/076,180.

Notice or Allowance dated Sep. 15, 2005 in U.S. Appl. No. 10/004,942, now US Patent No. 7,045,148.

Office Action dated Dec. 16, 2004 in U.S. Appl. No. 10/004,942, now US Patent No. 7,045,148.

Office Action dated Dec. 5, 2003 in U.S. Appl. No. 10/004,942, now US Patent No. 7,045,148.

Office Action dated Jun. 15, 2004 in U.S. Appl. No. 10/004,942, now US Patent No. 7,045,148.

Office Action dated Jun. 20, 2005 in U.S. Appl. No. 10/004,942, now US Patent No. 7,045,148.

Office Action dated May 7, 2003, in U.S. Appl. No. 10/004,942, now US Patent No. 7,045,148.

Notice of Allowance dated Aug. 16, 2007 in U.S. Appl. No. 10/074,976, now US Patent No. 7,311,904.

Office Action dated Jan. 5, 2006 in U.S. Appl. No. 10/074,976, now US Patent No. 7,311,904.

Office Action dated Mar. 22, 2007 in U.S. Appl. No. 10/074,976, now US Patent No. 7,311,904.

Office Action dated Sep. 20, 2006, in U.S. Appl. No. 10/074,976, now US Patent No. 7,311,904.

Office Action dated Sep. 23, 2004 in U.S. Appl. No. 10/074,976, now US Patent No. 7,311,904.

(56) References Cited

OTHER PUBLICATIONS

Notice of Allowance dated Sep. 10, 2007 in U.S. Appl. No. 10/366,671, now US Patent No. 7,311,905.
Office Action dated Jan. 19, 2006 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Advisory Action dated Feb. 2, 2007 in U.S. Appl. No. 10/366,671, now US Patent No. 7,311,905.
Advisory Action dated Jun. 6, 2006 in U.S. Appl. No. 10/779,369.
Final Office Action dated Nov. 7, 2005 in U.S. Appl. No. 10/779,369.
Office Action dated Mar. 29, 2005 in U.S. Appl. No. 10/779,369.
Notice of Allowance May 21, 2007 in U.S. Appl. No. 10/640,428, now US Patent No. 7,255,879.
Office Action dated Jan. 19, 2006 in U.S. Appl. No. 10/640,428 now Patent No. 7,255,879.
Office Action dated Oct. 18, 2006 in U.S. Appl. No. 10/640,428 now Patent No. 7,255,879.
Notice of Allowance dated Oct. 14, 2008 in U.S. Appl. No. 10/874,828, now US Patent No. 7,468,276.
Office Action dated Apr. 6, 2007 in U.S. Appl. No. 10/874,828, now US Patent No. 7,468,276.
Office Action dated Dec. 13, 2007 in U.S. Appl. No. 10/874,828, now US Patent No. 7,468,276.
Office Action dated Jun. 12, 2006 in U.S. Appl. No. 10/874,828, now US Patent No. 7,468,276.
Office Action dated Sep. 9, 2008 in U.S. Appl. No. 10/874,828, now US Patent No. 7,468,276.
Notice of Allowance dated Aug. 12, 2009 in U.S. Appl. No. 11/187,400.
Office Action dated Feb. 20, 2009 in U.S. Appl. No. 11/187,400.
Advisory Action dated Sep. 8, 2008 in U.S. Appl. No. 11/187,400.
Office Action dated Jan. 4, 2008 in U.S. Appl. No. 11/187,400.
Office Action dated May 22, 2008 in U.S. Appl. No. 11/187,400.
Office Action dated Apr. 20, 2007 in U.S. Appl. No. 11/187,400.
Office Action dated Apr. 2, 2009 in U.S. Appl. No. 10/721,144.
Non Final Office Action dated Feb. 1, 2011 in U.S. Appl. No. 10/721,144.
Final Office Action dated Sep. 14, 2010 in U.S. Appl. No. 10/721,144.
Office Action dated Mar. 18, 2010 in U.S. Appl. No. 10/721,144.
Advisory Action dated Oct. 7, 2009 in U.S. Appl. No. 10/721,144.
Advisory Action dated Aug. 17, 2009 in U.S. Appl. No. 10/721,144.
Office Action dated Feb. 5, 2008 in U.S. Appl. No. 10/721,144.
Final Office Action dated Jun. 27, 2007 in U.S. Appl. No. 10/721,144.
Office Action dated Dec. 28, 2006 in U.S. Appl. No. 10/721,144.
Office Action dated Jun. 14, 2006 in U.S. Appl. No. 10/721,144.
Advisory Action dated Feb. 6, 2006 in U.S. Appl. No. 10/721,144.
Final Office Action dated Jan. 11, 2006 in U.S. Appl. No. 10/721,144.
Office Action dated Oct. 4, 2005 in U.S. Appl. No. 10/721,144.
Final Office Action dated Aug. 4, 2010 in U.S. Appl. No. 11/592,544.
Non Final Office Action dated Feb. 4, 2009 in U.S. Appl. No. 11/592,544.
Notice of Allowance dated Jan. 10, 2011 in U.S. Appl. No. 11/648,813.
Non Final Office Action dated Jun. 7, 2010 in U.S. Appl. No. 11/648,813.
Final Office Action dated Oct. 27, 2009 in U.S. Appl. No. 11/648,813.
Office Action dated Jan. 26, 2009 in U.S. Appl. No. 11/648,813.
Final Office Action dated May 20, 2010 in U.S. Appl. No. 11/648,804.
Non-Final Office Action dated Oct. 21, 2009 in U.S. Appl. No. 11/648,804.
Final Office Action dated Feb. 7, 2011 in U.S. Appl. No. 12/030,161.
Non Final Office Action dated May 26, 2010 in U.S. Appl. No. 12/030,161.
Final Office Action dated Feb. 1, 2011 in U.S. Appl. No. 11/982,291.
Non Final Office Action dated Jul. 15, 2010 in U.S. Appl. No. 11/982,291.
Notice of Allowance dated Nov. 29, 2010 in U.S. Appl. No. 11/980,012.
Non Final Office Action dated Jun. 7, 2010 in U.S. Appl. No. 11/980,012.
Final Office Action dated Jan. 28, 2011 in U.S. Appl. No. 11/982,007.
Non Final Office Action dated Jul. 9, 2010 in U.S. Appl. No. 11/982,007.
Final Office Action dated Nov. 3, 2010 in U.S. Appl. No. 11/982,211.
Non Final Office Action dated May 24, 2010 in U.S. Appl. No. 11/982,211.
Final Office Action dated Nov. 3, 2010 in U.S. Appl. No. 12/030,170.
Non Final Office Action dated Jun. 4, 2010 in U.S. Appl. No. 12/030,170.
Non Final Office Action dated Dec. 15, 2009 in U.S. Appl. No. 12/030,170.
Non Final Office Action dated Jul. 9, 2010 in U.S. Appl. No. 12/259,259.
Notice of Allowance dated Apr. 21, 2011 in U.S. Appl. No. 12/341,961.
Non Final Office Action dated Sep. 1, 2010 in U.S. Appl. No. 12/341,961.
Notice of Allowance dated Feb. 18, 2011 in U.S. Appl. No. 12/341,961.
Extended Search Report mailed Mar. 25, 2011 in Application No. EP 10182243.5-2401.

\* cited by examiner

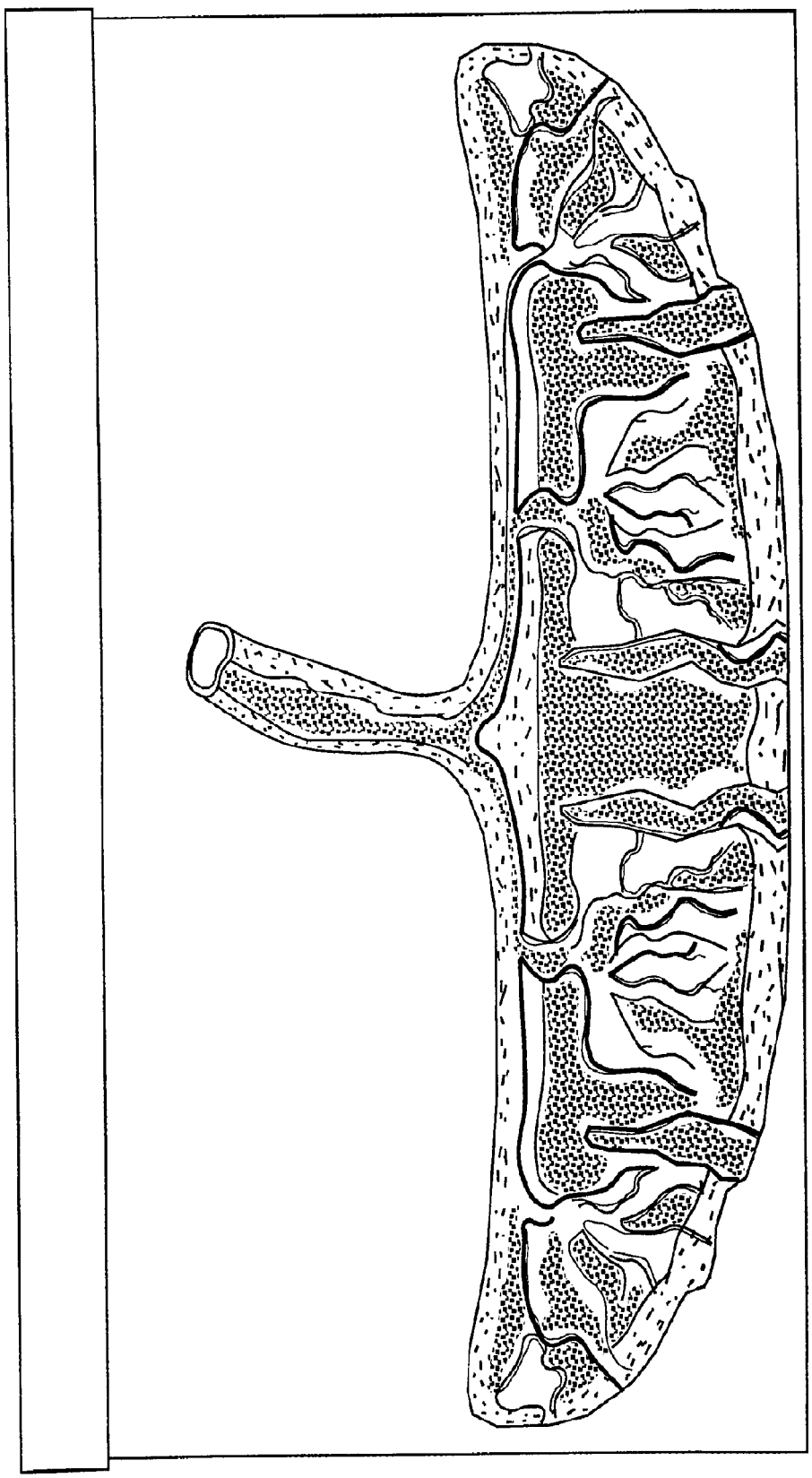
FIG. 2e  Drained, Perfused Placenta Stored in Air-Tight Container

TREATMENT OF DISEASES OR DISORDERS USING PLACENTAL STEM CELLS

This application is a continuation of U.S. patent application Ser. No. 12/341,961, filed Dec. 22, 2008, now U.S. Pat. No. 7,976,836, which is a continuation of U.S. patent application Ser. No. 12/259,259, filed Oct. 27, 2008, each of which is a continuation of U.S. patent application Ser. No. 10/874,828, filed Jun. 22, 2004, now U.S. Pat. No. 7,468,276, which is a continuation of U.S. patent application Ser. No. 10/076,180, filed Feb. 13, 2002, now abandoned, which claims benefit of U.S. Provisional Application No. 60/268,560, filed Feb. 14, 2001, and which is a continuation-in-part of U.S. patent application Ser. No. 10/004,942, filed Dec. 5, 2001, now U.S. Pat. No. 7,045,148, which claims benefit of U.S. Provisional Application No. 60/251,900, filed Dec. 6, 2000, each of which is hereby incorporated by reference herein in its entirety.

1. INTRODUCTION

The present invention relates to methods of exsanguinating and perfusing a placenta following expulsion from the uterus, e.g., after birth. The present invention relates to methods of treating and culturing an isolated placenta for the propagation of embryonic-like stem cells originating from the placenta and exogenous sources. The present invention further relates to the use of a cultured placenta as a bioreactor to produce biological materials or culture cells, tissues and organoids. The present invention also relates to stem cell collection and propagation, and in particular, to the collection of embryonic-like stem cells and other multipotent stem cells from placentas. The present invention relates to embryonic-like stem cells originating from a post-partum placenta.

2. BACKGROUND OF THE INVENTION

There is considerable interest in the identification, isolation and generation of human stem cells. Human stem cells are totipotential or pluripotential precursor cells capable of generating a variety of mature human cell lineages. This ability serves as the basis for the cellular differentiation and specialization necessary for organ and tissue development.

Recent success at transplanting such stem cells have provided new clinical tools to reconstitute and/or supplement bone marrow after myeloablation due to disease, exposure to toxic chemical and/or radiation. Further evidence exists that demonstrates that stem cells can be employed to repopulate many, if not all, tissues and restore physiologic and anatomic functionality. The application of stem cells in tissue engineering, gene therapy delivery and cell therapeutics is also advancing rapidly.

Many different types of mammalian stem cells have been characterized. For example, embryonic stem cells, embryonic germ cells, adult stem cells or other committed stem cells or progenitor cells are known. Certain stem cells have not only been isolated and characterized but have also been cultured under conditions to allow differentiation to a limited extent. A basic problem remains, however, in that obtaining sufficient quantities and populations of human stem cells which are capable of differentiating into all cell types is near impossible. Stem cells are in critically short supply. These are important for the treatment of a wide variety of disorders, including malignancies, inborn errors of metabolism, hemoglobinopathies, and immunodeficiencies. It would be highly advantageous to have a source of more embryonic stem cells.

Obtaining sufficient numbers of human stem cells has been problematic for several reasons. First, isolation of normally occurring populations of stem cells in adult tissues has been technically difficult and costly due, in part, to very limited quantity found in blood or tissue. Secondly, procurement of these cells from embryos or fetal tissue, including abortuses, has raised religious and ethical concerns. The widely held belief that the human embryo and fetus constitute independent life has prompted governmental restrictions on the use of such sources for all purposes, including medical research. Alternative sources that do not require the use of cells procured from embryonic or fetal tissue are therefore essential for further progress in the use of stem cells clinically. There are, however, few viable alternative sources of stem cells, particularly human stem cells, and thus supply is limited. Furthermore, harvesting of stem cells from alternative sources in adequate amounts for therapeutic and research purposes is generally laborious, involving, e.g., harvesting of cells or tissues from a donor subject or patient, culturing and/or propagation of cells in vitro, dissection, etc.

For example, Caplan et al. (U.S. Pat. No. 5,486,359 entitled "Human mesenchymal stem cells," issued Jan. 23, 1996), discloses human mesenchymal stem cell (hMSC) compositions derived from the bone marrow that serve as the progenitors for mesenchymal cell lineages. Caplan et al. discloses that hMSCs are identified by specific cell surface markers that are identified with monoclonal antibodies. Homogeneous hMSC compositions are obtained by positive selection of adherent marrow or periosteal cells that are free of markers associated with either hematopoietic cell or differentiated mesenchymal cells. These isolated mesenchymal cell populations display epitopic characteristics associated with mesenchymal stem cells, have the ability to regenerate in culture without differentiating, and have the ability to differentiate into specific mesenchymal lineages when either induced in vitro or placed in vivo at the site of damaged tissue. The drawback of such methods, however, is that they require harvesting of marrow or periosteal cells from a donor, from which the MSCs must be subsequently isolated.

Hu et al. (WO 00/73421 entitled "Methods of isolation, cryopreservation, and therapeutic use of human amniotic epithelial cells," published Dec. 7, 2000) discloses human amniotic epithelial cells derived from placenta at delivery that are isolated, cultured, cryopreserved for future use, or induced to differentiate. According to Hu et al., a placenta is harvested immediately after delivery and the amniotic membrane separated from the chorion, e.g., by dissection. Amniotic epithelial cells are isolated from the amniotic membrane according to standard cell isolation techniques. The disclosed cells can be cultured in various media, expanded in culture, cryopreserved, or induced to differentiate. Hu et al. discloses that amniotic epithelial cells are multipotential (and possibly pluripotential), and can differentiate into epithelial tissues such as corneal surface epithelium or vaginal epithelium. The drawback of such methods, however, is that they are labor-intensive and the yield of stem cells is very low. For example, to obtain sufficient numbers of stem cells for typical therapeutic or research purposes, amniotic epithelial cells must be first isolated from the amnion by dissection and cell separation techniques, then cultured and expanded in vitro.

Umbilical cord blood (cord blood) is a known alternative source of hematopoietic progenitor stem cells. Stem cells from cord blood are routinely cryopreserved for use in hematopoietic reconstitution, a widely used therapeutic procedure used in bone marrow and other related transplantations (see e.g., Boyse et al., U.S. Pat. No. 5,004,681, "Preservation of Fetal and Neonatal Hematopoietin Stem and Progenitor Cells of the Blood", Boyse et al., U.S. Pat. No. 5,192,553, entitled "Isolation and preservation of fetal and neonatal hematopoietic stem and progenitor cells of the blood and methods of therapeutic use", issued Mar. 9, 1993). Conventional techniques for the collection of cord blood are based on the use of a needle or cannula, which is used with the aid of gravity to drain cord blood from (i.e., exsanguinate) the placenta (Boyse et al., U.S. Pat. No. 5,192,553, issued Mar. 9, 1993; Boyse et al., U.S. Pat. No. 5,004,681, issued Apr. 2, 1991; Anderson, U.S. Pat. No. 5,372,581, entitled Method and apparatus for placental blood collection, issued Dec. 13, 1994; Hessel et al., U.S. Pat. No. 5,415,665, entitled Umbilical cord clamping, cutting, and blood collecting device and method, issued May 16, 1995). The needle or cannula is usually placed in the umbilical vein and the placenta is gently massaged to aid in draining cord blood from the placenta. Thereafter, however, the drained placenta has been regarded as having no further use and has typically been discarded. A major limitation of stem cell procurement from cord blood, moreover, has been the frequently inadequate volume of cord blood obtained, resulting in insufficient cell numbers to effectively reconstitute bone marrow after transplantation.

Naughton et al. (U.S. Pat. No. 5,962,325 entitled "Three-dimensional stromal tissue cultures" issued Oct. 5, 1999) discloses that fetal cells, including fibroblast-like cells and chondrocyte-progenitors, may be obtained from umbilical cord or placenta tissue or umbilical cord blood. Naughton et al. (U.S. Pat. No. 5,962,325) discloses that such fetal stromal cells can be used to prepare a "generic" stromal or cartilaginous tissue. Naughton et al. also discloses that a "specific" stromal tissue may be prepared by inoculating a three-dimensional matrix with fibroblasts derived from a particular individual who is later to receive the cells and/or tissues grown in culture in accordance with the disclosed methods. The drawback of such an approach however, is that it is labor intensive. According to the methods disclosed in Naughton et al., to recover fetal stromal cells from the umbilical cord or placenta requires dissection of these tissues, mincing of the tissue into pieces and disaggregation. Furthermore, to obtain adequate amounts of the fetal stromal cells from umbilical cord blood, as well as the umbilical cord and placenta, requires further expansion ex vivo.

Currently available methods for the ex vivo expansion of cell populations are also labor-intensive. For example, Emerson et al. (Emerson et al., U.S. Pat. No. 6,326,198 entitled "Methods and compositions for the ex vivo replication of stem cells, for the optimization of hematopoietic progenitor cell cultures, and for increasing the metabolism, GM-CSF secretion and/or IL-6 secretion of human stromal cells", issued Dec. 4, 2001); discloses methods, and culture media conditions for ex vivo culturing of human stem cell division and/or the optimization of human hematopoietic progenitor stem cells. According to the disclosed methods, human stem cells or progenitor cells derived from bone marrow are cultured in a liquid culture medium that is replaced, preferably perfused, either continuously or periodically, at a rate of 1 ml of medium per ml of culture per about 24 to about 48 hour period. Metabolic products are removed and depleted nutrients replenished while maintaining the culture under physiologically acceptable conditions.

Kraus et al. (Kraus et al., U.S. Pat. No. 6,338,942, entitled "Selective expansion of target cell populations", issued Jan. 15, 2002) discloses that a predetermined target population of cells may be selectively expanded by introducing a starting sample of cells from cord blood or peripheral blood into a growth medium, causing cells of the target cell population to divide, and contacting the cells in the growth medium with a selection element comprising binding molecules with specific affinity (such as a monoclonal antibody for CD34) for a predetermined population of cells (such as CD34 cells), so as to select cells of the predetermined target population from other cells in the growth medium.

Rodgers et al. (U.S. Pat. No. 6,335,195 entitled "Method for promoting hematopoietic and mesenchymal cell proliferation and differentiation," issued Jan. 1, 2002) discloses methods for ex vivo culture of hematopoietic and mesenchymal stem cells and the induction of lineage-specific cell proliferation and differentiation by growth in the presence of angiotensinogen, angiotensin I (AI), AI analogues, AI fragments and analogues thereof, angiotensin II (AII), AII analogues, AII fragments or analogues thereof or AII $AT_2$ type 2 receptor agonists, either alone or in combination with other growth factors and cytokines. The stem cells are derived from bone marrow, peripheral blood or umbilical cord blood. The drawback of such methods, however, is that such ex vivo methods for inducing proliferation and differentiation of stem cells are time-consuming, as discussed above, and also result in low yields of stem cells.

Naughton et al., (U.S. Pat. No. 6,022,743 entitled "Three-dimensional culture of pancreatic parenchymal cells cultured living stromal tissue prepared in vitro," issued Feb. 8, 2000) discloses a tissue culture system in which stem cells or progenitor cells (e.g., stromal cells such as those derived from umbilical cord cells, placental cells, mesenchymal stem cells or fetal cells) are propagated on three-dimensional support rather than as a two-dimensional monolayer in, e.g., a culture vessel such as a flask or dish.

Because of restrictions on the collection and use of stem cells, and the inadequate numbers of cells typically collected from cord blood, stem cells are in critically short supply. Stem cells have the potential to be used in the treatment of a wide variety of disorders, including malignancies, inborn errors of metabolism, hemoglobinopathies, and immunodeficiencies. There is a critical need for a readily accessible source of large numbers of human stem cells for a variety of therapeutic and other medically related purposes. The present invention addresses that need and others.

3. SUMMARY OF THE INVENTION

The present invention relates to a mammalian placenta, preferably human, which following expulsion from the uterus has been treated and cultured to produce multipotent stem cells (e.g., committed progenitor cells), embryonic-like stem cells and other biological materials. In particular, the present invention provides methods of perfusing and exsanguinating a placenta post birth. The present invention provides methods of exsanguinating and perfusing a placenta under sterile conditions for a period of at least two to greater than forty-eight hours following expulsion of the placenta from the uterus. In a preferred embodiment, the placenta is perfused with a solution containing factors to enhance the exsanguination, such as anticoagulant factors. In another embodiment, the placenta is perfused with a solution containing factors to enhance the sterile conditions, such as antimicrobial and antiviral agents. In a preferred embodiment, the placenta is perfused with a solution containing growth factors. Such solutions which contains growth factors and other culture components but without anticoagulants are referred to as culture solution.

In another preferred embodiment of the invention, the placenta is perfused to remove blood, residual cells, proteins and any other residual material. The placenta may be further processed to remove material debris. Perfusion is normally continued with an appropriate perfusate for at least two to more than twenty-four hours. In several additional embodiments, of the invention, the placenta is perfused for at least 2, 4, 6, 8, 10, 12, 14, 16, 18, 20, and 22 hours prior to the collection of stem cells. The perfusate collected from any of these time points may also provide a source of embryonic-like stem cells. It should be understood that the first collection of blood from the placenta is referred to as cord blood which contains predominantly CD34+ and CD38+ hematopoietic progenitor cells. Within the first twenty-four hours of post-partum perfusion, CD34+ and CD38− hematopoietic progenitor cells can be isolated from the placenta along with CD34+ and CD38− cells. After about twenty-four hours of perfusion, CD34− and CD38− cells can be isolated from the placenta along with the aforementioned cells.

The present invention relates to an isolated placenta that has been exsanguinated and perfused under sterile conditions. In a preferred embodiment, the invention provides an isolated placenta that has been exsanguinated and perfused to remove all residual cells and cultured for a period of two to twenty four hours following expulsion from the uterus. The present invention also provides an isolated placenta that has been treated and cultured to result in a viable organ capable of producing embryonic-like stem cells, progenitor cells and other biological materials.

The present invention relates to a stem cell producing apparatus which comprises a post-partum mammalian placenta which has been exsanguinated and perfused, a means for incubating or culturing the placenta; and a means for detecting stem cells. In another embodiment, the apparatus of the invention further comprises a collection device and/or a means for separating the collected cells. In another embodiment, the apparatus of the invention further comprises a means for monitoring and adjusting the culture conditions and collection of cells.

The present invention also provides methods of incubating and culturing an isolated exsanguinated placenta under the appropriate conditions to allow for the production of embryonic-like stem cells that originate from the placenta. In accordance with the present invention, embryonic-like stem cells are obtained from a placenta following expulsion from the uterus. The placenta is exsanguinated and perfused for a period of at least two to twenty four hours to remove all residual cells. The exsanguinated placenta is then cultured under the appropriate conditions to allow for the production of endogenous stem cells originating from the placenta, including, but not limited to embryonic-like stem cells, and pluripotent or multipotent stem cells. In a preferred embodiment, the exsanguinated placenta is cultured in the presence of growth factors, such as PDGF and EGF.

The present invention further provides methods of treating and culturing an isolated placenta for use as a bioreactor for the propagation of endogenous stem cells originating from the placenta. The present invention provides methods of treating and culturing an isolated placenta for use as a bioreactor for the propagation of exogenous cells and biological materials, e.g., antibodies, proteins, oligonucleotides, hormones, viruses, cytokines and enzymes. The present invention also provides propagation and collection of embryonic-like stem cells and other pluripotent and multipotent stem cells from placentas. The cultured placenta may be used repeatedly as a bioreactor and may be cultured over a period of days, months and even years. The cultured placenta may be maintained by periodically or continuously removing a portion of a culture medium or perfusion fluid that is introduced into the system and from which the propagated cells or produced biological materials may be recovered, and replaced with fresh medium or perfusate liquid.

In another embodiment, the invention provides a method of utilizing the isolated and perfused placenta as a bioreactor in which to propagate endogenous cells, including, but not limited to, embryonic-like stem cells, progenitor cells, pluripotent cells and multipotent cells. The endogenous cells propagated in the placental bioreactor may be collected, and/or bioactive molecules recovered from the perfusate, culture medium or from the placenta cells themselves.

In another embodiment, the invention provides a method of utilizing the isolated and perfused placenta as a bioreactor in which to propagate exogenous cells. In accordance with this embodiment, the invention relates to an isolated placenta which contains a cell not derived from the placenta, wherein the engraftment of said cell into the placenta may stimulate the placenta to produce embryonic-like stem cells or wherein the engrafted cell produces signals, such a cytokines and growth factors, which may stimulate the placenta to produce stem cells. In accordance with this embodiment, the placenta may be engrafted with cells not placental in origin obtained from the infant associated with the placenta. In another embodiment, the placenta may be engrafted with cells not placental in origin obtained from the parents or siblings of the infant associated with the placenta. The exogenous cells propagated in the placental bioreactor may be collected, and/or bioactive molecules recovered from the perfusate, culture medium or from the placenta cells themselves.

The present invention provides embryonic-like stem cells that originate from a placenta. The embryonic-like stem cells of the invention may be characterized by measuring changes in morphology and cell surface markers using techniques such as flow cytometry and immunocytochemistry, and measuring changes in gene expression using techniques, such as PCR. In one embodiment of the invention, such embryonic-like stem cells may be characterized by the presence of the following cell surface markers: CD10+, CD29+, CD34−, CD38−, CD44+, CD45−, CD54+, CD90+, SH2+, SH3+, SH4+, SSEA3−, SSEA4−, OCT-4+, and ABC-p+. In a preferred embodiment, such embryonic-like stem cells may be characterized by the presence of cell surface markers OCT-4+ and APC-p+. Embryonic-like stem cells originating from placenta the have characteristics of embryonic stem cells but are not derived from the embryo. In other words, the invention encompasses OCT-4+ and ABC-p+ cells that are undifferentiated stem cells that are isolated from post-partum perfused placenta. Such cells are as versatile (e.g., pluripotent) as human embryonic stem cells. As mentioned above, a number of different pluripotent or multipotent stem cells can be isolated from the perfused placenta at different time points e.g., CD34+/CD38+, CD34+/CD38−, and CD34−/CD38− hematopoietic cells. According to the methods of the invention, human placenta is used post-birth as the source of embryonic-like stem cells.

In another embodiment, the invention provides a method for isolating other embryonic-like and/or multipotent or pluripotent stem cells from an extractant or perfusate of a exsanguinated placenta.

The present invention relates to pharmaceutical compositions which comprise the embryonic-like stem cells of the invention. The present invention further relates to an isolated homogenous population of human placental stem cells which has the potential to differentiate into all cell types. The invention also encompasses pharmaceutical compositions have high concentrations (or larger populations) of homogenous hematopoietic stem cells including but not limited to CD34+/CD38− cells; and CD34−/CD38− cells one or more of these cell populations can be used with or as a mixture with cord blood hematopoietic cells i.e., CD34+/CD38+ hematopoietic cells for transplantation and other uses.

The stem cells obtained by the methods of the invention have a multitude of uses in transplantation to treat or prevent disease. In one embodiment of the invention, they are used to renovate and repopulate tissues and organs, thereby replacing or repairing diseased tissues, organs or portions thereof.

3.1. DEFINITIONS

As used herein, the term "bioreactor" refers to an ex vivo system for propagating cells, producing or expressing biological materials and growing or culturing cells tissues, organoids, viruses, proteins, polynucleotides and microorganisms.

As used herein, the term "embryonic stem cell" refers to a cell that is derived from the inner cell mass of a blastocyst (e.g., a 4- to 5-day-old human embryo) and that is pluripotent.

As used herein, the term "embryonic-like stem cell" refers to a cell that is not derived from the inner cell mass of a blastocyst. As used herein, an "embryonic-like stem cell" may also be referred to as a "placental stem cell." An embryonic-like stem cell is preferably pluripotent. However, the stem cells which may be obtained from the placenta include embryonic-like stem cells, multipotent cells, and committed progenitor cells. According to the methods of the invention, embryonic-like stem cells derived from the placenta may be collected from the isolated placenta once it has been exsanguinated and perfused for a period of time sufficient to remove residual cells.

As used herein, the term "exsanguinated" or "exsanguination," when used with respect to the placenta, refers to the removal and/or draining of substantially all cord blood from the placenta. In accordance with the present invention, exsanguination of the placenta can be achieved by, for example, but not by way of limitation, draining, gravity induced efflux, massaging, squeezing, pumping, etc. In a preferred embodiment, exsanguination of the placenta may further be achieved by perfusing, rinsing or flushing the placenta with a fluid that may or may not contain agents, such as anticoagulants, to aid in the exsanguination of the placenta.

As used herein, the term "perfuse" or "perfusion" refers to the act of pouring or passaging a fluid over or through an organ or tissue, preferably the passage of fluid through an organ or tissue with sufficient force or pressure to remove any residual cells, e.g., non-attached cells from the organ or tissue. As used herein, the term "perfusate" refers to the fluid collected following its passage through an organ or tissue. In a preferred embodiment, the perfusate contains one or more anticoagulants.

As used herein, the term "exogenous cell" refers to a "foreign" cell, i.e., a heterologous cell (i.e., a "non-self" cell derived from a source other than the placental donor) or autologous cell (i.e., a "self" cell derived from the placental donor) that is derived from an organ or tissue other than the placenta.

As used herein, the term "organoid" refers to an aggregation of one or more cell types assembled in superficial appearance or in actual structure as any organ or gland of a mammalian body, preferably the human body.

As used herein, the term "multipotent cell" refers to a cell that has the capacity to grow into any of subset of the mammalian body's approximately 260 cell types. Unlike a pluripotent cell, a multipotent cell does not have the capacity to form all of the cell types.

As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), an embryonic stem cell cannot usually form a new blastocyst.

As used herein, the term "progenitor cell" refers to a cell that is committed to differentiate into a specific type of cell or to form a specific type of tissue.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells.

As used herein, the term "totipotent cell" refers to a cell that is able to form a complete embryo (e.g., a blastocyst).

4. BRIEF DESCRIPTION OF THE FIGURES

FIG. 1 is a cross-sectional view of the cannulation of the vein and artery of a placenta to perfuse the placenta and then collect the perfusate.

FIGS. 2a-e are schematics showing the collection, clamping, perfusion, collection and storage of an exsanguinated and perfused placenta.

5. DETAILED DESCRIPTION OF THE INVENTION

Figure 1:
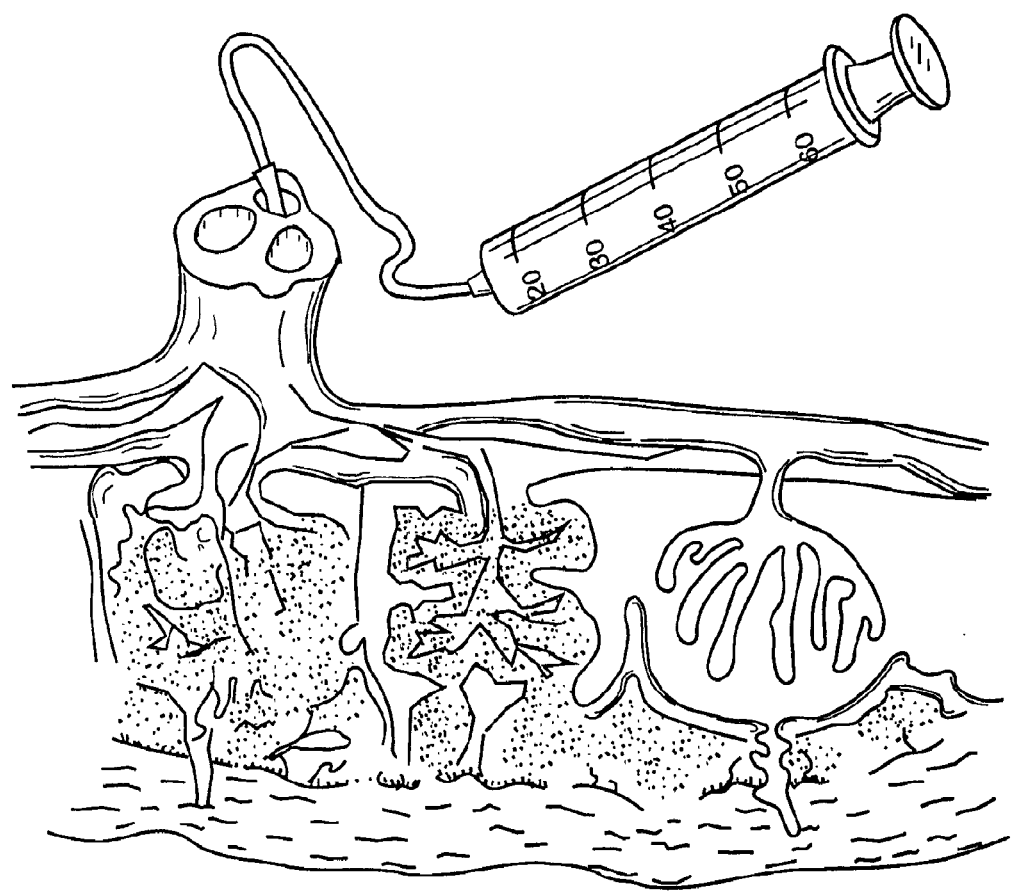
Figure 2A:
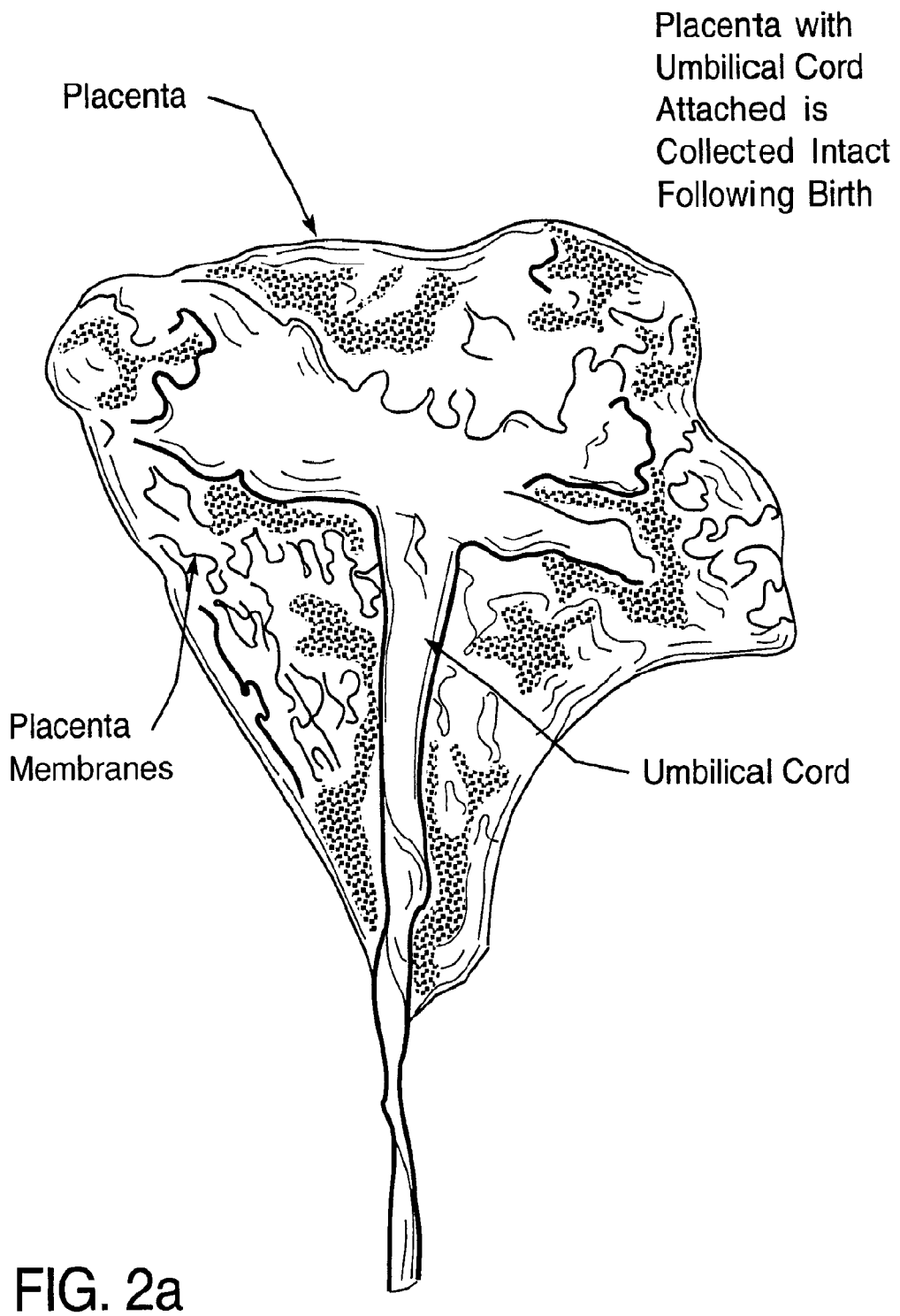
Figure 2B:
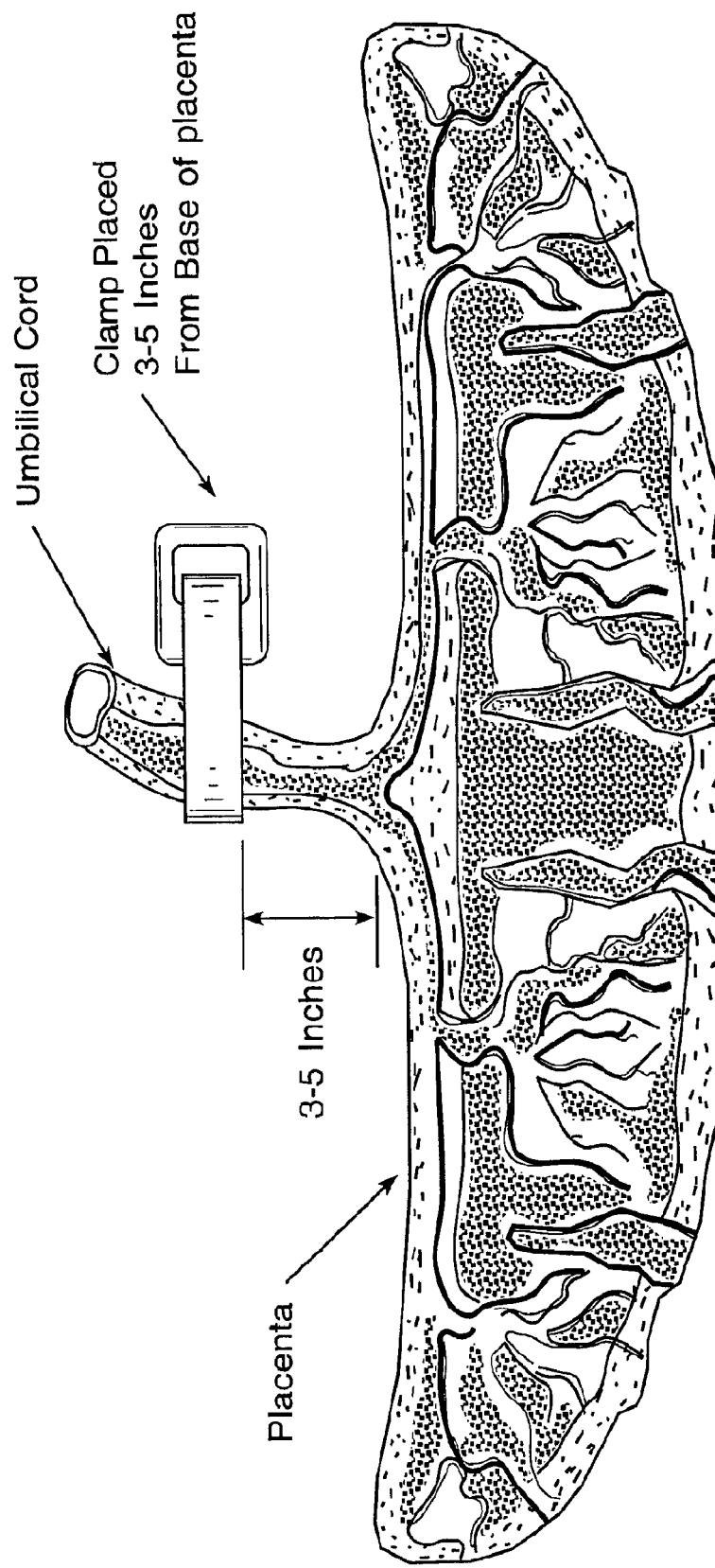
Figure 2C:
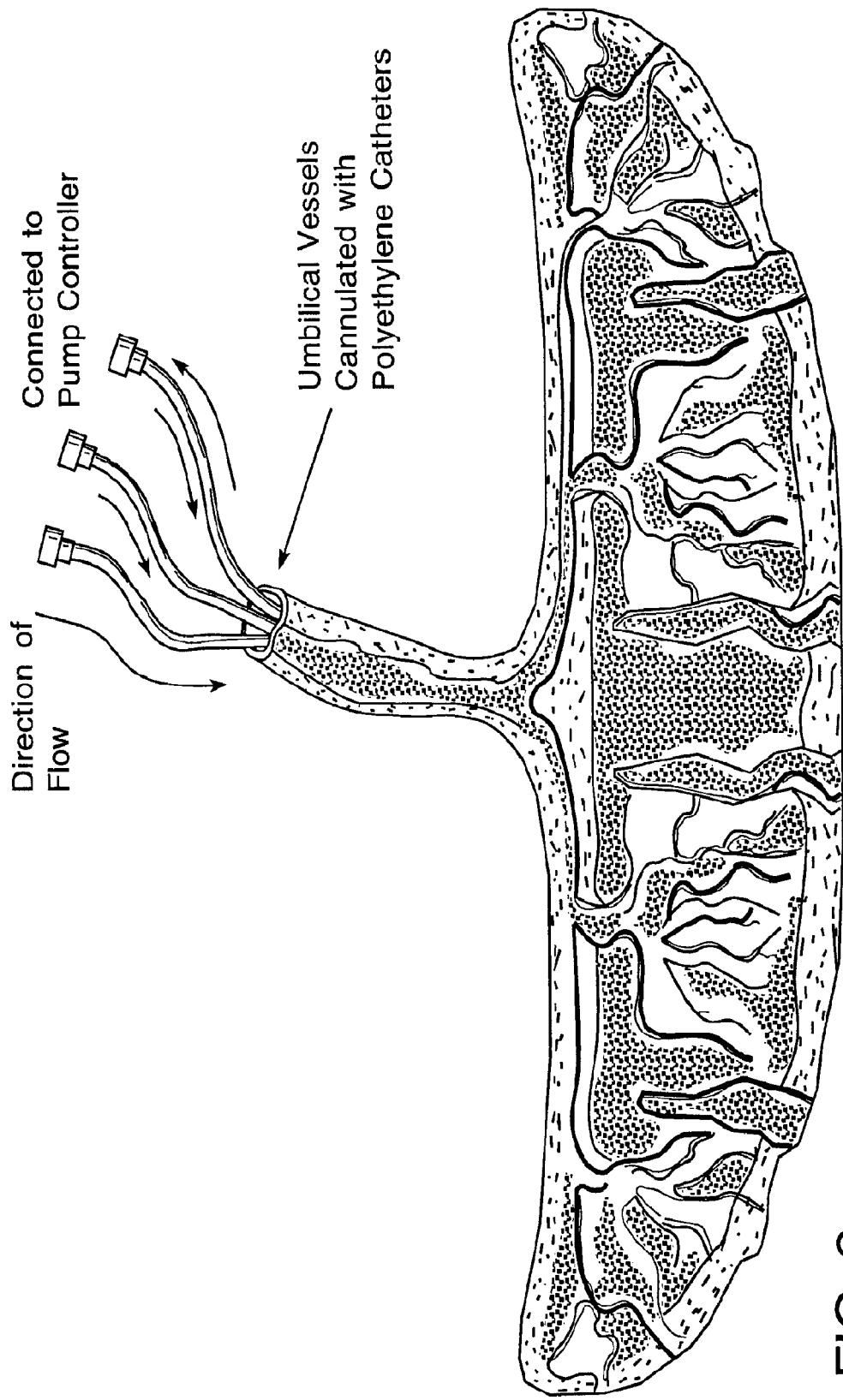
Figure 2D:
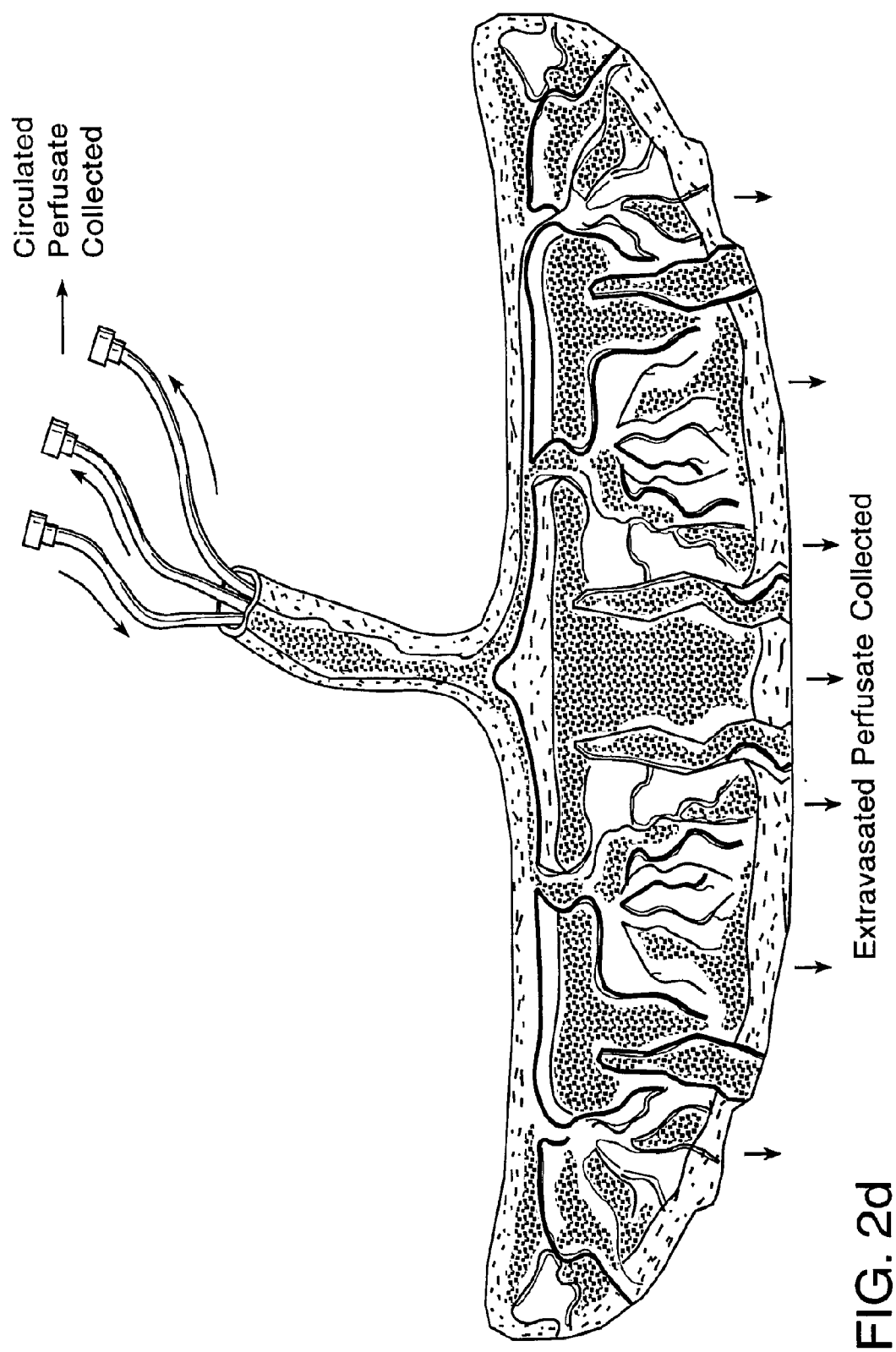

The applicant has unexpectedly discovered that the placenta after birth contains quiescent cells which can be activated if the placenta is properly processed after birth. For example, after expulsion from the womb, the placenta is exsanguinated as quickly as possible to prevent or minimize apoptosis. Subsequently, as soon as possible after exsanguination the placenta is perfused to remove blood, residual cells, proteins, factors and any other materials present in the organ. Materials debris may also be removed from the placenta. Perfusion is normally continued with an appropriate perfusate for at least two to more than twenty-four hours. In several additional embodiments the placenta is perfused for at least 4, 6, 8, 10, 12, 14, 16, 18, 20, and 22 hours. In other words, this invention is based at least in part on the discovery that the cells of a post-partum placenta can be activated by exsanguination and perfusion for a sufficient amount of time. Therefore, the placenta can readily be used as a rich and abundant source of embryonic-like stem cells, which cells can be used for research, including drug discovery, treatment and prevention of diseases, in particular transplantation surgeries or therapies, and the generation of committed cells, tissues and organoids.

Further, surprisingly and unexpectedly the human placental stem cells produced by the exsanguinated, perfused and/or cultured placenta are pluripotent stem cells that can readily be differentiated into any desired cell type.

The present invention relates to methods of treating and culturing an isolated placenta for use as a bioreactor for the production and propagation of embryonic-like stem cells originating from the placenta or from exogenous sources. The present invention also relates to the use of a cultured placenta as a bioreactor to produce biological materials, including, but not limited to, antibodies, hormones, cytokines, growth factors and viruses. The present invention also relates to methods of collecting and isolating the stem cells and biological materials from the cultured placenta.

The present invention relates to methods of perfusing and exsanguinating an isolated placenta once it has been expunged from a uterus, to remove all residual cells. The invention further relates to culturing the isolated and exsanguinated placenta under the appropriate conditions to allow for the production and propagation of embryonic-like stem cells.

The present invention provides a method of extracting and recovering embryonic-like stem cells, including, but not limited to pluripotent or multipotent stem cells, from an exsanguinated human placenta. Embryonic-like stem cells have characteristics of embryonic stem cells but are not derived from the embryo. Such cells are as versatile (e.g., pluripotent) as human embryonic stem cells. According to the methods of the invention, human placenta is used post-birth as the source of embryonic-like stem cells.

According to the methods of the invention embryonic-like stem cells are extracted from a drained placenta by means of a perfusion technique that utilizes either or both of the umbilical artery and umbilical vein. The placenta is preferably drained by exsanguination and collection of residual blood (e.g., residual umbilical cord blood). The drained placenta is then processed in such a manner as to establish an ex vivo, natural bioreactor environment in which resident embryonic-like stem cells within the parenchyma and extravascular space are recruited. The embryonic-like stem cells migrate into the drained, empty microcirculation where, according to the methods of the invention, they are collected, preferably by washing into a collecting vessel by perfusion.

5.1. Methods of Isolating and Culturing Placenta 5.1.1. Pretreatment of Placenta According to the methods of the invention, a human placenta is recovered shortly after its expulsion after birth and, in certain embodiments, the cord blood in the placenta is recovered. In certain embodiments, the placenta is subjected to a conventional cord blood recovery process. Such cord blood recovery may be obtained commercially, e.g., LifeBank Inc., Cedar Knolls, N.J., ViaCord, Cord Blood Registry and Cryo-cell. The cord blood can be drained shortly after expulsion of the placenta.

Postpartum the placenta is drained of cord blood. The placenta stored may be under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood.

Typically, a placenta is transported from the delivery or birthing room to another location, e.g., a laboratory, for recovery of the cord blood and/or drainage and perfusion. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container, as shown in FIGS. 2a-e. Preferably, the placenta is delivered to the laboratory four to twenty-four hours following delivery.

The placenta is preferably recovered after expulsion under aseptic conditions, and stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (1% w/w in 1:1000 solution). The drained placenta is preferably stored for no more than 36 hours before the embryonic-like stem cells are collected. The solution which is used to perfuse the placenta to remove residual cells can be the same solution used to perfuse and culture the placenta for the recovery of stem cells. Any of these perfusates may be collected and used as a source of embryonic-like stem cells.

In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

Conventional techniques for the collection of cord blood may be used. Typically a needle or cannula is used, with the aid of gravity, to drain cord blood from (i.e., exsanguinate) the placenta (Boyse et al., U.S. Pat. No. 5,192,553, issued Mar. 9, 1993; Boyse et al., U.S. Pat. No. 5,004,681, issued Apr. 2, 1991; Anderson, U.S. Pat. No. 5,372,581, entitled Method and apparatus for placental blood collection, issued Dec. 13, 1994; Hessel et al., U.S. Pat. No. 5,415,665, entitled Umbilical cord clamping, cutting, and blood collecting device and method, issued May 16, 1995). The needle or cannula is usually placed in the umbilical vein and the placenta is gently massaged to aid in draining cord blood from the placenta.

In a preferred embodiment, the placenta is recovered from a patient by informed consent and a complete medical history of the patient prior to, during and after pregnancy is also taken and is associated with the placenta. These medical records can be used to coordinate subsequent use of the placenta or the stem cells harvested therefrom. For example, the human placental stem cells can then easily be used for personalized medicine for the infant in question, the parents, siblings or other relatives. Indeed, the human placental stem cells are more versatile than cord blood. However, it should be noted that the invention includes the addition of human placental stem cells produced by the exsanguinated, perfused and/or cultured placenta to cord blood from the same or different placenta and umbilical cord. The resulting cord blood will have an increased concentration/population of human stem cells and thereby is more useful for transplantation e.g. for bone marrow transplantations.

5.1.2. Exsanguination of Placenta and Removal of Residual Cells

The invention provides a method for recovery of stem or progenitor cells, including, but not limited to embryonic-like stem cells, from a placenta that is exsanguinated, i.e., completely drained of the cord blood remaining after birth and/or a conventional cord blood recovery procedure. According to the methods of the invention, the placenta is exsanguinated and perfused with a suitable aqueous perfusion fluid, such as an aqueous isotonic fluid in which an anticoagulant (e.g., heparin, warfarin sodium) is dissolved. Such aqueous isotonic fluids for perfusion are well known in the art, and include, e.g., a 0.9 N sodium chloride solution. The perfusion fluid preferably comprises the anticoagulant, such as heparin or warfarin sodium, at a concentration that is sufficient to prevent the formation of clots of any residual cord blood. In a specific embodiment, a concentration of from 1 to 100 units of heparin is employed, preferably a concentration of 1 to 10 units of heparin per ml is employed. In one embodiment, apoptosis inhibitors, such as free radical scavengers, in particular oxygen free radical scavengers, can be used during and immediately after exsanguination and then these agents can be washed from the placenta. In accordance with this embodiment of the invention, the isolated placenta may be stored under hypothermic conditions in order to prevent or inhibit apoptosis.

According to the methods of the invention, the placenta is exsanguinated by passage of the perfusion fluid through either or both of the umbilical artery and umbilical vein, using a gravity flow into the placenta. The placenta is preferably oriented (e.g., suspended) in such a manner that the umbilical artery and umbilical vein are located at the highest point of the placenta. In a preferred embodiment, the umbilical artery and the umbilical vein are connected simultaneously, as shown in FIG. 1, to a pipette that is connected via a flexible connector to a reservoir of the perfusion fluid. The perfusion fluid is passed into the umbilical vein and artery and collected in a suitable open vessel from the surface of the placenta that was attached to the uterus of the mother during gestation. The perfusion fluid may also be introduced through the umbilical cord opening and allowed to flow or percolate out of openings in the wall of the placenta which interfaced with the maternal uterine wall.

In a preferred embodiment, the proximal umbilical cord is clamped during perfusion, and more preferably, is clamped within 4-5 cm (centimeter) of the cord's insertion into the placental disc.

In one embodiment, a sufficient amount of perfusion fluid is used that will result in removal of all residual cord blood and subsequent collection or recovery of placental cells, including but not limited to embryonic-like stem cells and progenitor cells, that remain in the placenta after removal of the cord blood.

It has been observed that when perfusion fluid is first collected from a placenta during the exsanguination process, the fluid is colored with residual red blood cells of the cord blood. The perfusion fluid tends to become clearer as perfusion proceeds and the residual cord blood cells are washed out of the placenta. Generally from 30 to 100 ml (milliliter) of perfusion fluid is adequate to exsanguinate the placenta and to recover an initial population of embryonic-like cells from the placenta, but more or less perfusion fluid may be used depending on the observed results.

5.1.3. Culturing Placenta

After exsanguination and a sufficient time of perfusion of the placenta, the embryonic-like stem cells are observed to migrate into the exsanguinated and perfused microcirculation of the placenta where, according to the methods of the invention, they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

In certain embodiments of the invention, the drained, exsanguinated placenta is cultured as a bioreactor, i.e., an ex vivo system for propagating cells or producing biological materials. The number of propagated cells or level of biological material produced in the placental bioreactor is maintained in a continuous state of balanced growth by periodically or continuously removing a portion of a culture medium or perfusion fluid that is introduced into the placental bioreactor, and from which the propagated cells or the produced biological materials may be recovered. Fresh medium or perfusion fluid is introduced at the same rate or in the same amount.

The number and type of cells propagated may easily be monitored by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, or by measuring changes in gene expression using techniques well known in the art, such as PCR and gene expression profiling.

In one embodiment, the cells may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In another embodiment, magnetic beads can be used to separate cells. The cells may be sorted using a magnetic activated cell sorting (MACS) technique, a method for separating particles based on their ability to bind magnetic beads (0.5-100 µm diameter). A variety of useful modifications can be performed on the magnetic microspheres, including covalent addition of antibody which specifically recognizes a cell-solid phase surface molecule or hapten. A magnetic field is then applied, to physically manipulate the selected beads. The beads are then mixed with the cells to allow binding. Cells are then passed through a magnetic field to separate out cells having cell surface markers. These cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

In preferred embodiments, the placenta to be used as a bioreactor is exsanguinated and washed under sterile conditions so that any adherent coagulated and non-adherent cellular contaminants are removed. The placenta is then cultured or cultivated under aseptic conditions in a container or other suitable vessel, and perfused with perfusate solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml).

The effluent perfusate comprises both circulated perfusate, which has flowed through the placental circulation, and extravasated perfusate, which exudes from or passes through the walls of the blood vessels into the surrounding tissues of the placenta. The effluent perfusate is collected, and preferably, both the circulated and extravasated perfusates are collected, preferably in a sterile receptacle. Alterations in the conditions in which the placenta is maintained and the nature of the perfusate can be made to modulate the volume and composition of the effluent perfusate.

Cell types are then isolated from the collected perfusate by employing techniques known by those skilled in the art, such as for example, but not limited to density gradient centrifugation, magnet cell separation, flow cytometry, affinity cell separation or differential adhesion techniques.

Figure 3:
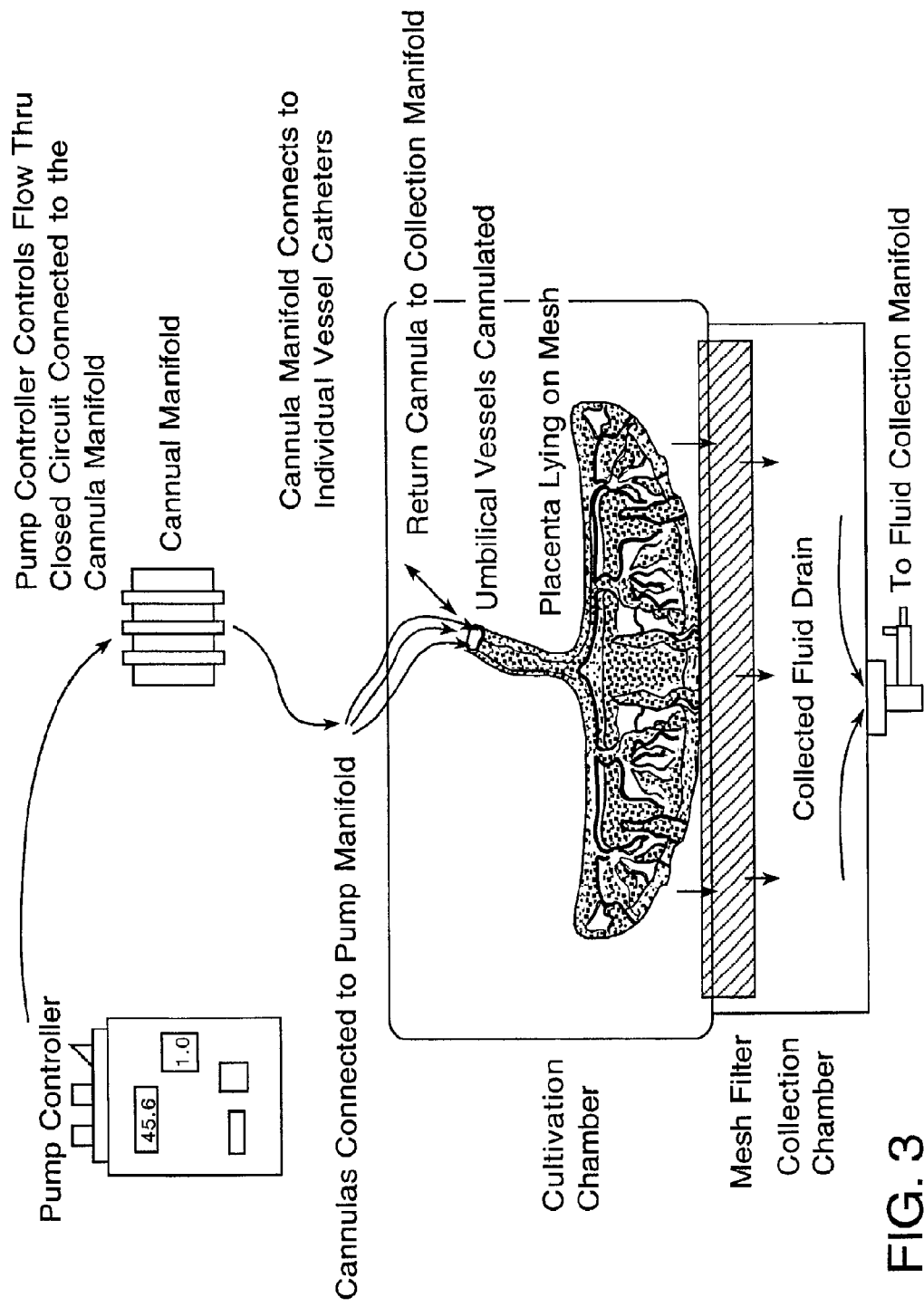
FIG. 3 is a cross-sectional schematic of a perfused placenta in a device for use as a bioreactor.

In one embodiment, a placenta is placed in a sterile basin and washed with 500 ml of phosphate-buffered normal saline. The wash fluid is then discarded. The umbilical vein is then cannulated with a cannula, e.g., a TEFLON® or plastic cannula, that is connected to a sterile connection apparatus, such as sterile tubing. The sterile connection apparatus is connected to a perfusion manifold, as shown in FIG. 3. The container containing the placenta is then covered and the placenta is maintained at room temperature (20-25° C.) for a desired period of time, preferably from 2 to 24 hours, and preferably, no longer than 48 hours. The placenta may be perfused continually, with equal volumes of perfusate introduced and effluent perfusate removed or collected. Alternatively, the placenta may be perfused periodically, e.g., at every 2 hours or at 4, 8, 12, and 24 hours, with a volume of perfusate, e.g., 100 ml of perfusate (sterile normal saline supplemented with or without 1000 u/l heparin and/or EDTA and/or CPDA (creatine phosphate dextrose)). In the case of periodic perfusion, preferably equal volumes of perfusate are introduced and removed from the culture environment of the placenta, so that a stable volume of perfusate bathes the placenta at all times.

The effluent perfusate that escapes the placenta, e.g., at the opposite surface of the placenta, is collected and processed to isolate embryonic-like stem cells, progenitor cells or other cells of interest.

Various media may be used as perfusion fluid for culturing or cultivating the placenta, such as DMEM, F-12, M199, RPMI, Fisher's, Iscore's, McCoy's and combinations thereof, supplemented with fetal bovine serum (FBS), whole human serum (WHS), or human umbilical cord serum collected at the time of delivery of the placenta. The same perfusion fluid used to exsanguinate the placenta of residual cord blood may be used to culture or cultivate the placenta, without the addition of anticoagulant agents.

In certain embodiments, the embryonic-like stem cells are induced to propagate in the placenta bioreactor by introduction of nutrients, hormones, vitamins, growth factors, or any combination thereof, into the perfusion solution. Serum and other growth factors may be added to the propagation perfusion solution or medium. Growth factors are usually proteins and include, but are not limited to: cytokines, lymphokines, interferons, colony stimulating factors (CSF's), interferons, chemokines, and interleukins. Other growth factors that may be used include recombinant human hematopoietic growth factors including ligands, stem cell factors, thrombopoeitin (Tpo), granulocyte colony-stimulating factor (G-CSF), leukemia inhibitory factor, basic fibroblast growth factor, placenta derived growth factor and epidermal growth factor.

The growth factors introduced into the perfusion solution can stimulate the propagation of undifferentiated embryonic-like stem cells, committed progenitor cells, or differentiated cells (e.g., differentiated hematopoietic cells). The growth factors can stimulate the production of biological materials and bioactive molecules including, but not limited to, immunoglobulins, hormones, enzymes or growth factors as previously described.

In one embodiment of the invention, the placenta is used as a bioreactor for propagating endogenous cells (i.e., cells that originate from the placenta), including but not limited to, various kinds of pluripotent and/or totipotent embryonic-like stem cells and lymphocytes. To use the placenta as a bioreactor, it may be cultured for varying periods of time under sterile conditions by perfusion with perfusate solution as disclosed herein. In specific embodiments, the placenta is cultured for at least 12, 24, 36, or 48 hours, or for 3-5 days, 6-10 days, or for one to two weeks. In a preferred embodiment, the placenta is cultured for 48 hours. The cultured placenta should be "fed" periodically to remove the spent media, depopulate released cells, and add fresh media. The cultured placenta should be stored under sterile conditions to reduce the possibility of contamination, and maintained under intermittent and periodic pressurization to create conditions that maintain an adequate supply of nutrients to the cells of the placenta. It should be recognized that the perfusing and culturing of the placenta can be both automated and computerized for efficiency and increased capacity.

In another embodiment, the placenta is processed to remove all endogenous proliferating cells, such as embryonic-like stem cells, and to allow foreign (i.e., exogenous) cells to be introduced and propagated in the environment of the perfused placenta. The invention contemplates a large variety of stem or progenitor cells that can be cultured in the placental bioreactor, including, but not limited to, embryonic-like stem cells, mesenchymal stem cells, stromal cells, endothelial cells, hepatocytes, keratinocytes, and stem or progenitor cells for a particular cell type, tissue or organ, including but not limited to neurons, myelin, muscle, blood, bone marrow, skin, heart, connective tissue, lung, kidney, liver, and pancreas (e.g., pancreatic islet cells).

Sources of mesenchymal stem cells include bone marrow, embryonic yolk sac, placenta, umbilical cord, fetal and adolescent skin, and blood. Bone marrow cells may be obtained from iliac crest, femora, tibiae, spine, rib or other medullary spaces.

Methods for the selective destruction, ablation or removal of proliferating or rapidly dividing cells from a tissue or organ are well-known in the art, e.g., methods of cancer or tumor treatment. For example, the perfused placenta may be irradiated with electromagnetic, UV, X-ray, gamma- or beta-radiation to eradicate all remaining viable, endogenous cells. The foreign cells to be propagated are introduced into the irradiated placental bioreactor, for example, by perfusion.

5.2. Collection of Cells from the Placenta

As disclosed above, after exsanguination and perfusion of the placenta, embryonic-like stem cells migrate into the drained, empty microcirculation where, according to the methods of the invention, they are collected, preferably by collecting the effluent perfusate in a collecting vessel.

Figure 4:
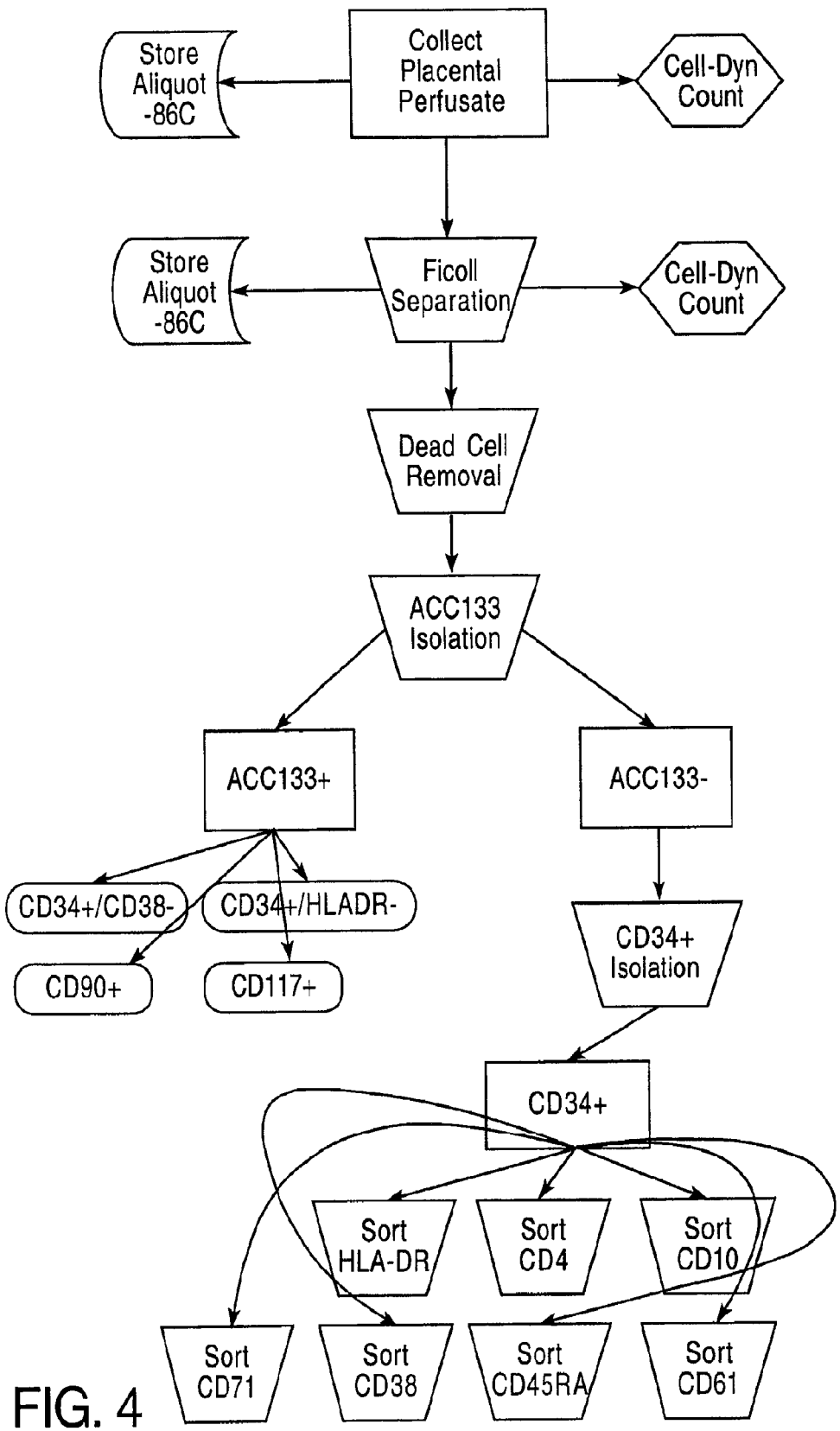
FIG. 4 is a selection scheme for sorting cells, including embryonic-like stem cells, retrieved from a perfused placenta.

In preferred embodiments, cells cultured in the placenta are isolated from the effluent perfusate using techniques known by those skilled in the art, such as, for example, density gradient centrifugation, magnet cell separation, flow cytometry, or other cell separation or sorting methods well known in the art, and sorted, for example, according to the scheme shown in FIG. 4.

In a specific embodiment, cells collected from the placenta are recovered from the effluent perfusate by centrifugation at 5000×g for 15 minutes at room temperature, which separates cells from contaminating debris and platelets. The cell pellets are resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of cells is achieved by "differential trypsinization," using a solution of 0.05% trypsin with 0.2% EDTA (Sigma, St. Louis Mo.). Differential trypsinization was possible because fibroblastoid cells detached from plastic surfaces within about five minutes whereas the other adherent populations required more than 20-30 minutes incubation.

The detached fibroblastoid cells were harvested following trypsinization and trypsin neutralization, using Trypsin Neutralizing Solution (TNS, BioWhittaker). The cells were washed in H.DMEM and resuspended in MSCGM.

In another embodiment, the isolated placenta is perfused for a period of time without collecting the perfusate, such that the placenta may be perfused for 2, 4, 6, 8, 10, 12, 20 and 24 hours or even days before the perfusate is collected.

In another embodiment, cells cultured in the placenta bioreactor are isolated from the placenta by physically dissecting the cells away from the placenta.

In another embodiment, cells cultured in the placenta bioreactor are isolated from the placenta by dissociating the tissues of the placenta or a portion thereof, and recovering the cultured cells by art-known cell separation or sorting methods such as density gradient centrifugation, magnet cell separation, flow cytometry, etc.

In a preferred embodiment, perfusion of the placenta and collection of effluent perfusate is repeated once or twice during the culturing of the placenta, until the number of recovered nucleated cells falls below 100 cells/ml. The perfusates are pooled and subjected to light centrifugation to remove platelets, debris and de-nucleated cell membranes. The nucleated cells are then isolated by Ficoll-Hypaque density gradient centrifugation and after washing, resuspended in H.DMEM. For isolation of the adherent cells, aliquots of $5\text{-}10 \times 10^6$ cells are placed in each of several T-75 flasks and cultured with commercially available Mesenchymal Stem Cell Growth Medium (MSCGM) obtained from BioWhittaker, and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

In other embodiments, the cells collected from the placenta are cryopreserved for use at a later time. Methods for cryopreservation of cells, such as stem cells, are well known in the art, for example, cryopreservation using the methods of Boyse et al. (U.S. Pat. No. 5,192,553, issued Mar. 9, 1993) or Hu et al. (WO 00/73421, published Dec. 7, 2000).

5.3. Cell Populations Obtained from or Cultured in Placenta

Embryonic-like stem cells obtained in accordance with the methods of the invention may include pluripotent cells, i.e., cells that have complete differentiation versatility, that are self-renewing, and can remain dormant or quiescent within tissue. The stem cells which may be obtained from the placenta include embryonic-like stem cells, multipotent cells, committed progenitor cells, and fibroblastoid cells.

The first collection of blood from the placenta is referred to as cord blood which contains predominantly CD34+ and CD38+ hematopoietic progenitor cells. Within the first twenty-four hours of post-partum perfusion, high concentrations of CD34+ and CD38− hematopoietic progenitor cells may be isolated from the placenta, along with high concentrations of CD34− and CD38+ hematopoietic progenitor cells. After about twenty-four hours of perfusion, high concentrations of CD34− and CD38− cells can be isolated from the placenta along with the aforementioned cells. The isolated perfused placenta of the invention provides a source of large quantities of stem cells enriched for CD34+ and CD38− stem cells and CD34− and CD38+ stem cells. The isolated placenta which has been perfused for twenty-four hours or more provides a source of large quantities of stem cells enriched for CD34− and CD38− stem cells.

In a preferred embodiment, embryonic-like stem cells obtained by the methods of the invention are viable, quiescent, pluripotent stem cells that exist within a full-term human placenta and that can be recovered following successful birth and placental expulsion, resulting in the recovery of as many as one billion nucleated cells, which yield 50-100 million multipotent and pluripotent stem cells.

The human placental stem cells provided by the placenta are surprisingly embryonic-like, for example, the presence of the following cell surface markers have been identified for these cells: SSEA3−, SSEA4−, OCT-4+ and ABC-p+. Preferably, the embryonic-like stem cells of the invention are characterized by the presence of OCT-4+ and ABC-p+ cell surface markers. Thus, the invention encompasses stem cells which have not been isolated or otherwise obtained from an embryonic source but which can be identified by the following markers: SSAE3−, SSAE4−, OCT-4+ and ABC-p+. In one embodiment, the human placental stem cells do not express MHC Class 2 antigens.

The stem cells isolated from the placenta are homogenous, and sterile. Further, the stem cells are readily obtained in a form suitable for administration to humans, i.e., they are of pharmaceutical grade.

Preferred embryonic-like stem cells obtained by the methods of the invention may be identified by the presence of the following cell surface markers: OCT-4+ and ABC-pt. Further, the invention encompasses embryonic stem cells having the following markers: CD10+, CD38−, CD29+, CD34−, CD44+, CD45−, CD54+, CD90+, SH2+, SH3+, SH4+, SSEA3−, SSEA4−, OCT-4+, and ABC-p+. Such cell surface markers are routinely determined according to methods well known in the art, e.g. by flow cytometry, followed by washing and staining with an anti-cell surface marker antibody. For example, to determine the presence of CD-34 or CD-38, cells may be washed in PBS and then double-stained with anti-CD34 phycoerythrin and anti-CD38 fluorescein isothiocyanate (Becton Dickinson, Mountain View, Calif.).

In another embodiment, cells cultured in the placenta bioreactor are identified and characterized by a colony forming unit assay, which is commonly known in the art, such as MesenCult™ medium (stem cell Technologies, Inc., Vancouver British Columbia)

The embryonic-like stem cells obtained by the methods of the invention may be induced to differentiate along specific cell lineages, including adipogenic, chondrogenic, osteogenic, hematopoietic, myogenic, vasogenic, neurogenic, and hepatogenic. In certain embodiments, embryonic-like stem cells obtained according to the methods of the invention are induced to differentiate for use in transplantation and ex vivo treatment protocols. In certain embodiments, embryonic-like stem cells obtained by the methods of the invention are induced to differentiate into a particular cell type and genetically engineered to provide a therapeutic gene product. In a specific embodiment, embryonic-like stem cells obtained by the methods of the invention are incubated with a compound in vitro that induces it to differentiate, followed by direct transplantation of the differentiated cells to a subject. Thus, the invention encompasses methods of differentiating the human placental stem cells using standard culturing media. Further, the invention encompasses hematopoietic cells, neuron cells, fibroblast cells, strand cells, mesenchymal cells and hepatic cells.

Embryonic-like stem cells may also be further cultured after collection from the placenta using methods well known in the art, for example, by culturing on feeder cells, such as irradiated fibroblasts, obtained from the same placenta as the embryonic-like stem cells or from other human or nonhuman sources, or in conditioned media obtained from cultures of such feeder cells, in order to obtain continued long-term cultures of embryonic-like stem cells. The embryonic-like stem cells may also be expanded, either within the placenta before collection from the placental bioreactor or in vitro after recovery from the placenta. In certain embodiments, the embryonic-like stem cells to be expanded are exposed to, or cultured in the presence of, an agent that suppresses cellular differentiation. Such agents are well-known in the art and include, but are not limited to, human Delta-1 and human Serrate-1 polypeptides (see, Sakano et al., U.S. Pat. No. 6,337,387 entitled "Differentiation-suppressive polypeptide", issued Jan. 8, 2002), leukemia inhibitory factor (LIF) and stem cell factor. Methods for the expansion of cell populations are also known in the art (see e.g., Emerson et al., U.S. Pat. No. 6,326,198 entitled "Methods and compositions for the ex vivo replication of stem cells, for the optimization of hematopoietic progenitor cell cultures, and for increasing the metabolism, GM-CSF secretion and/or IL-6 secretion of human stromal cells", issued Dec. 4, 2001; Kraus et al., U.S. Pat. No. 6,338,942, entitled "Selective expansion of target cell populations", issued Jan. 15, 2002).

The embryonic-like stem cells may be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

In certain embodiments, the differentiation of stem cells or progenitor cells that are cultivated in the exsanguinated, perfused and/or cultured placenta is modulated using an agent or pharmaceutical compositions comprising a dose and/or doses effective upon single or multiple administration, to exert an effect sufficient to inhibit, modulate and/or regulate the differentiation of a cell collected from the placenta.

Agents that can induce stem or progenitor cell differentiation are well known in the art and include, but are not limited to, $Ca^{2+}$, EGF, aFGF, bFGF, PDGF, keratinocyte growth factor (KGF), TGF-$\beta$, cytokines (e.g., IL-1$\alpha$, IL-1$\beta$, IFN-$\gamma$, TFN), retinoic acid, transferrin, hormones (e.g., androgen, estrogen, insulin, prolactin, triiodothyronine, hydrocortisone, dexamethasone), sodium butyrate, TPA, DMSO, NMF, DMF, matrix elements (e.g., collagen, laminin, heparan sulfate, Matrigel™), or combinations thereof.

Agents that suppress cellular differentiation are also well-known in the art and include, but are not limited to, human Delta-1 and human Senate-1 polypeptides (see, Sakano et al., U.S. Pat. No. 6,337,387 entitled "Differentiation-suppressive polypeptide", issued Jan. 8, 2002), leukemia inhibitory factor (LIF), and stem cell factor.

The agent used to modulate differentiation can be introduced into the placental bioreactor to induce differentiation of the cells being cultured in the placenta. Alternatively, the agent can be used to modulate differentiation in vitro after the cells have been collected or removed from the placenta.

Determination that a stem cell has differentiated into a particular cell type may be accomplished by methods well-known in the art, e.g., measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the art, such as PCR and gene-expression profiling.

In another embodiment, the cells cultured in the placenta are stimulated to produce bioactive molecules, such as immunoglobulins, hormones, enzymes.

In another embodiment, the cells cultured in the placenta are stimulated to proliferate, for example, by administration of erythropoietin, cytokines, lymphokines, interferons, colony stimulating factors (CSF's), interferons, chemokines, interleukins, recombinant human hematopoietic growth factors including ligands, stem cell factors, thrombopoeitin (Tpo), interleukins, and granulocyte colony-stimulating factor (G-CSF) or other growth factors.

In another embodiment, cells cultured in the placenta are genetically engineered either prior to, or after collection from, the placenta, using, for example, a viral vector such as an adenoviral or retroviral vector, or by using mechanical means such as liposomal or chemical mediated uptake of the DNA.

A vector containing a transgene can be introduced into a cell of interest by methods well known in the art, e.g., transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter, such that the transgene is transmitted to daughter cells, e.g., the daughter embryonic-like stem cells or progenitor cells produced by the division of an embryonic-like stem cell. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

Preferably, the transgene is introduced using any technique, so long as it is not destructive to the cell's nuclear membrane or other existing cellular or genetic structures. In certain embodiments, the transgene is inserted into the nucleic genetic material by microinjection. Microinjection of cells and cellular structures is commonly known and practiced in the art.

For stable transfection of cultured mammalian cells, such as cells culture in a placenta, only a small fraction of cells may integrate the foreign DNA into their genome. The efficiency of integration depends upon the vector and transfection technique used. In order to identify and select integrants, a gene that encodes a selectable marker (e.g., for resistance to antibiotics) is generally introduced into the host embryonic-like stem cell along with the gene sequence of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die). Such methods are particularly useful in methods involving homologous recombination in mammalian cells (e.g., in embryonic-like stem cells) prior to introduction or transplantation of the recombinant cells into a subject or patient.

A number of selection systems may be used to select transformed host embryonic-like cells. In particular, the vector may contain certain detectable or selectable markers. Other methods of selection include but are not limited to selecting for another marker such as: the herpes simplex virus thymidine kinase (Wigler et al., 1977, Cell 11: 223), hypoxanthine-guanine phosphoribosyltransferase (Szybalska and Szybalski, 1962, Proc. Natl. Acad. Sci. USA 48: 2026), and adenine phosphoribosyltransferase (Lowy et al., 1980, Cell 22: 817)

genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan and Berg, 1981, Proc. Natl. Acad. Sci. USA 78: 2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30: 147).

The transgene may integrate into the genome of the cell of interest, preferably by random integration. In other embodiments the transgene may integrate by a directed method, e.g., by directed homologous recombination (i.e., "knock-in" or "knock-out" of a gene of interest in the genome of cell of interest), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996).

Methods for generating cells having targeted gene modifications through homologous recombination are known in the art. The construct will comprise at least a portion of a gene of interest with a desired genetic modification, and will include regions of homology to the target locus, i.e., the endogenous copy of the targeted gene in the host's genome. DNA constructs for random integration, in contrast to those used for homologous recombination, need not include regions of homology to mediate recombination. Markers can be included in the targeting construct or random construct for performing positive and negative selection for insertion of the transgene.

To create a homologous recombinant cell, e.g., a homologous recombinant embryonic-like stem cell, endogenous placental cell or exogenous cell cultured in the placenta, a homologous recombination vector is prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, Cell 51: 503; Bradley, 1991, Curr. Opin. Bio/Technol. 2: 823-29; and PCT Publication Nos. WO 90/11354, WO 91/01140, and WO 93/04169.

In one embodiment, the genome of an exogenous cell cultured in the placenta according to the methods of the invention is a target of gene targeting via homologous recombination or via random integration.

In a specific embodiment, the methods of Bonadio et al. (U.S. Pat. No. 5,942,496, entitled Methods and compositions for multiple gene transfer into bone cells, issued Aug. 24, 1999; and PCT WO95/22611, entitled Methods and compositions for stimulating bone cells, published Aug. 24, 1995) are used to introduce nucleic acids into a cell of interest, such as a stem cell, progenitor cell or exogenous cell cultured in the placenta, e.g., bone progenitor cells.

5.4 Uses of Cultured Placenta as a Bioreactor

Exsanguinated and/or cultured placental cells can be used as a bioreactor for the cultivation of cells, tissues, and organs. The placental mesoderm provides an ideal stromal environment, including an abundance of small molecules and growth factors, lipopolysaccharides, and extracellular matrix proteins, necessary for organogenesis and tissue neogenesis.

In one embodiment, the invention provides a method of utilizing the isolated perfused placenta as a bioreactor for the propagation of exogenous cells. In accordance with this embodiment, the invention relates to an isolated placenta which contains a cell not derived from the placenta, wherein the engraftment of said cell into the placenta may stimulate the placenta to produce embryonic-like stem cells, or wherein the engrafted cell produces signals, such as cytokines and growth factors, which may stimulate the placenta to produce stem cells. The placenta may be engrafted with cells not placental in origin obtained from the parents, siblings or other blood relatives of the infant associated with the placenta. In another embodiment, the isolated placenta may be engrafted with cells not placental in origin obtained from an individual whom is not the infant, nor related to the infant. Likewise, the cells, tissues, organoids and organs, which are propagated and cultivated in the placenta may be transplanted into the infant associated with the placenta, the parents, siblings or other blood relatives of said infant or into an individual not related to the infant.

In one embodiment of the invention, the placenta can be populated with any particular cell type and used as a bioreactor for ex vivo cultivation of cells, tissues or organs. Such cells, tissue or organ cultures may be harvested used in transplantation and ex vivo treatment protocols. In this embodiment, the placenta is processed to remove all endogenous cells and to allow foreign (i.e., exogenous) cells to be introduced and propagated in the environment of the perfused placenta. Methods for removal of the endogenous cells are well-known in the art. For example, the perfused placenta is irradiated with electromagnetic, UV, X-ray, gamma- or beta-radiation to eradicate all remaining viable, endogenous cells. In one embodiment, sub-lethal exposure to radiations e.g., 500 to 1500 CGγ can be used to preserve the placenta but eradicate undesired cells. For international on lethal v. non-lethal ionizing radiation (see Chapter 5 "Biophysical and Biological Effects of Ionizing Radiation" from the United States Department of Defense The foreign cells of interest to be propagated in the irradiated placental bioreactor are then introduced, for example, by vascular perfusion or direct intra-parenchymal injection.

In another embodiment, the bioreactor may be used to produce and propagate novel chimeric cells, tissues, or organs. Such chimeras may be created using placental cells and one or more additional cell types as starting materials in a bioreactor. The interaction, or "cross-talk" between the different cell types can induce expression patterns distinct from either of the starting cell types. In one embodiment, for example, an autologous chimera is generated by propagating a patient's autologous placental cells in a bioreactor with another cell type derived from the same patient. In another embodiment, for example, a heterologous chimera may be generated by addition of a patient's cells, i.e., blood cells, to a bioreactor having heterologous placental cells. In yet another embodiment, the placental cells may be derived from a patient, and a second cell type from a second patient. Chimeric cells are then recovered having a different phenotypic and/or genetic characteristics from either of the starting cells.

In a specific embodiment, the heterologous cells are of the same haplotype, and the chimeric cells are reintroduced into the patient.

In other embodiments, the bioreactor may be used for enhanced growth of a particular cell type, whether native or synthetic in origin, or for the production of a cell-type specific product. For example, in one embodiment, the placental bioreactor may be used to stimulate pancreatic islet cells to produce insulin. The bioreactor is particularly advantageous for production of therapeutic mammalian proteins, whose therapeutic efficacy can be dependent upon proper post-translational modification. Thus, the bioreactor is useful for the production of therapeutic proteins, growth factors, cytokines, and other natural or recombinant therapeutic molecules, such as but not limited to, erythropoietin, interleukins, and interferons.

In another embodiment, the bioreactor may be used to propagate genetically engineered cells to provide a therapeutic gene product, and employed for large-scale production of the recombinant product. In one embodiment, for example, the reactor may be used to enhance antibody production. The placenta may be populated with antibody-producing cells, such as hybridomas, which produce a specific monoclonal antibodies, which are homogeneous populations of antibodies to a particular antigen. Hybridomas may be obtained by any technique, including, but not limited to, the hybridoma technique of Kohler and Milstein (1975, Nature 256, 495-497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026-2030), and the EBV-hybridoma technique (Cole et al., 1985, Monoclonal Antibodies And Cancer Therapy, Alan R. Liss, Inc., pp. 77-96). The mAb-producing hybridomas may be cultivated in the bioreactor to produce high titers of mAbs.

Alternatively, where an antigen is unknown, the bioreactor may be used to generate antibodies specific for a particular cell-type, which may then be used identify the unknown antigen. For example, antibodies may be generated against an unknown tumor-specific antigen in a cancer patient by culturing a whole blood specimen from a cancer patient, expanding the cells in a bioreactor, and then screened for antibodies that specifically react against a patient's tumor cells.

In another embodiment, the bioreactor may be used to produce viruses in culture and for screening for antiviral agents in culture. This method is of particular interest for those viruses, such as parvovirus and human immunodeficiency virus, which are difficult to propagate in cell culture conditions.

The bioreactor may also be used as a support for screening for therapeutic molecules which modulate the activity of a particular cell type, such as the activity or expression of a gene product of interest or the activation of a signal transduction pathway. In this embodiment, a cell type of interest may be cultured and expanded in the bioreactor. The cell may be naturally occurring cell, or a cell engineered to express a recombinant gene product. The bioreactor is then be contacted with candidate therapeutic molecules, such as small molecules, nonpeptides, antibodies, etc., or libraries of such candidate therapeutic molecules. The cells are then analyzed for a change in a desired activity in the presence or absence of the candidate therapeutic molecule. For example, such desired activity might be an increase or decrease in growth rate, and change in gene expression, or a change in binding or uptake of the candidate therapeutic molecule.

Several types of methods are likely to be particularly convenient and/or useful for screening test agents. These include, but are not limited to, methods which measure binding of a compound, methods which measure a change in the ability cells to interact with an antibody or ligand, and methods which measure the activity or expression of "reporter" protein, that is, an enzyme or other detectable or selectable protein, which has been placed under the control of a control region of interest. Thus, in a preferred embodiment, both naturally occurring and/or synthetic compounds (e.g., libraries of small molecules or peptides), may be screened for therapeutic activity. The screening assays can be used to identify compounds and compositions including peptides and organic, non-protein molecules that modulate a cell-type specific activity. Recombinant, synthetic, and otherwise exogenous compounds may have binding capacity and, therefore, may be candidates for pharmaceutical agents. Alternatively, the proteins and compounds include endogenous cellular components which interact with the identified genes and proteins in vivo. Such endogenous components may provide new targets for pharmaceutical and therapeutic interventions.

In another embodiment of the invention, the placenta is used as a bioreactor for propagating endogenous cells (i.e., cells that originate from the placenta), including but not limited to, various kinds of pluripotent and/or totipotent embryonic-like stem cells and lymphocytes. In one embodiment, the placenta is incubated for varying periods of time with perfusate solution as disclosed herein. Such endogenous cells of placental origin may be transformed to recombinantly express a gene of interest, to express mutations, and/or may be engineered to delete a genetic locus, using "knock out" technology. For example, an endogenous target gene may be deleted by inactivating or "knocking out" the target gene or its promoter using targeted homologous recombination (e.g., see Smithies, et al., 1985, Nature 317, 230-234; Thomas & Capecchi, 1987, Cell 51, 503-512; Thompson, et al., 1989, Cell 5, 313-321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches may be used to remove, replace, or alter gene expression of interest in cells, tissue, and/or organs. This approach may be used to alter the phenotype of a cell, tissue, or organ, which may then be introduced into a human subject.

In other embodiments, a placenta cell may be induced to differentiate into a particular cell type, either ex vivo or in vivo. For example, pluripotent embryonic-like stem cells may be injected into a damaged organ, and for organ neogenesis and repair of injury in vivo. Such injury may be due to such conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis, ischemic renal disease, brain or spinal cord trauma, heart-lung bypass, glaucoma, retinal ischemia, or retinal trauma.

The embryonic-like stem cells isolated from the placenta may be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the cells may be used as autologous or heterologous transgene carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucoplysaccharide nosis, chronic granulomatous disease and tyrosinemia and Tay-Sachs disease or to treat cancer, tumors or other pathological conditions.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

The large numbers of embryonic-like stem cells and/or progenitor obtained using the methods of the invention would, in certain embodiments, reduce the need for large bone marrow donations. Approximately $1 \times 10^8$ to $2 \times 10^8$ bone marrow mononuclear cells per kilogram of patient weight must be infused for engraftment in a bone marrow transplantation (i.e., about 70 ml of marrow for a 70 kg donor). To obtain 70 ml requires an intensive donation and significant loss of blood in the donation process. In a specific embodiment, cells from a small bone marrow donation (e.g., 7-10 ml) could be expanded by propagation in a placental bioreactor before infusion into a recipient.

Furthermore, a small number of stem cells and progenitor cells normally circulate in the blood stream. In another embodiment, such exogenous stem cells or exogenous progenitor cells are collected by pheresis, a procedure in which blood is withdrawn, one or more components are selectively removed, and the remainder of the blood is reinfused into the donor. The exogenous cells recovered by pheresis are expanded by propagation in a placental bioreactor, thus eliminating the need for bone marrow donation entirely.

In another embodiment, expansion of exogenous cells in a placental bioreactor is used as a supplemental treatment in addition to chemotherapy. Most chemotherapy agents used to target and destroy cancer cells act by killing all proliferating cells, i.e., cells going through cell division. Since bone marrow is one of the most actively proliferating tissues in the body, hematopoietic stem cells are frequently damaged or destroyed by chemotherapy agents and in consequence, blood cell production is diminishes or ceases. Chemotherapy must be terminated at intervals to allow the patient's hematopoietic system to replenish the blood cell supply before resuming chemotherapy. It may take a month or more for the formerly quiescent stem cells to proliferate and increase the white blood cell count to acceptable levels so that chemotherapy may resume (when again, the bone marrow stem cells are destroyed).

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, embryonic-like stem cells or progenitor cells collected according to the methods of the invention could be introduced into the patient. Such treatment would reduce the time the patient would exhibit a low blood cell count, and would therefore permit earlier resumption of the chemotherapy treatment.

The embryonic-like stem cells, progenitor cells, foreign cells, or engineered cells obtained from a placenta according to the methods of the invention can be used in the manufacture of a tissue or organ in vivo. The methods of the invention encompass using cells obtained from the placenta, e.g., embryonic-like stem cells, progenitor cells, or foreign stem or progenitor cells, to seed a matrix and to be cultured under the appropriate conditions to allow the cells to differentiate and populate the matrix. The tissues and organs obtained by the methods of the invention may be used for a variety of purposes, including research and therapeutic purposes.

5.5 Uses of Embryonic-Like Stem Cells

The embryonic-like stem cells of the invention can be used for a wide variety of therapeutic protocols in which a tissue or organ of the body is augmented, repaired or replaced by the engraftment, transplantation or infusion of a desired cell population, such as a stem cell or progenitor cell population. The embryonic-like stem cells of the invention can be used to replace or augment existing tissues, to introduce new or altered tissues, or to join together biological tissues or structures. The embryonic-like stem cells of the invention can also be substituted for embryonic stem cells in therapeutic protocols in which embryonic stem cells would be typically be used.

In a preferred embodiment of the invention, embryonic-like stem cells and other stem cells from the placenta may be used as autologous and allogenic, including matched and mismatched HLA type hematopoietic transplants. In accordance with the use of embryonic-like stem cells as allogenic hematopoietic transplants it may be necessary to treat the host to reduce immunological rejection of the donor cells, such as those described in U.S. Pat. No. 5,800,539, issued Sep. 1, 1998; and U.S. Pat. No. 5,806,529, issued Sep. 15, 1998, both of which are incorporated herein by reference.

For example, embryonic-like stem cells of the invention can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Embryonic-like stem cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

Embryonic-like stem cells of the invention can be used for augmentation, repair or replacement of cartilage, tendon, or ligaments. For example, in certain embodiments, prostheses (e.g., hip prostheses) are coated with replacement cartilage tissue constructs grown from embryonic-like stem cells of the invention. In other embodiments, joints (e.g., knee) are reconstructed with cartilage tissue constructs grown from embryonic-like stem cells. Cartilage tissue constructs can also be employed in major reconstructive surgery for different types of joints (for protocols, see e.g., Resnick, D., and Niwayama, G., eds., 1988, Diagnosis of Bone and Joint Disorders, 2d ed., W. B. Saunders Co.).

The embryonic-like stem cells of the invention can be used to repair damage of tissues and organs resulting from disease. In such an embodiment, a patient can be administered embryonic-like stem cells to regenerate or restore tissues or organs which have been damaged as a consequence of disease, e.g., enhance immune system following chemotherapy or radiation, repair heart tissue following myocardial infarction.

The embryonic-like stem cells of the invention can be used to augment or replace bone marrow cells in bone marrow transplantation. Human autologous and allogenic bone marrow transplantation are currently used as therapies for diseases such as leukemia, lymphoma and other life-threatening disorders. The drawback of these procedures, however, is that a large amount of donor bone marrow must be removed to insure that there is enough cells for engraftment.

The embryonic-like stem cells collected according to the methods of the invention can provide stem cells and progenitor cells that would reduce the need for large bone marrow donation. It would also be, according to the methods of the invention, to obtain a small marrow donation and then expand the number of stem cells and progenitor cells culturing and expanding in the placenta before infusion or transplantation into a recipient.

The embryonic-like stem cells isolated from the placenta may be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's, Hunter's, Hurler's syndromes, as well as other gangliosidoses, mucopolysaccharidoses, and glycogenoses.

In other embodiments, the cells may be used as autologous or heterologous transgene carriers in gene therapy to correct inborn errors of metabolism such as adrenoleukodystrophy, cystic fibrosis, glycogen storage disease, hypothyroidism, sickle cell anemia, Pearson syndrome, Pompe's disease, phenylketonuria (PKU), and Tay-Sachs disease, porphyrias, maple syrup urine disease, homocystinuria, mucopolypsaccharide nosis, chronic granulomatous disease, and tyrosinemia. or to treat cancer, tumors or other pathological conditions.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, scalp (hair) transplantation, or for reconstruction of other damaged or diseased organs or tissues.

The large numbers of embryonic-like stem cells and/or progenitor obtained using the methods of the invention would, in certain embodiments, reduce the need for large bone marrow donations. Approximately $1 \times 10^8$ to $2 \times 10^8$ bone marrow mononuclear cells per kilogram of patient weight must be infused for engraftment in a bone marrow transplantation (i.e., about 70 ml of marrow for a 70 kg donor). To obtain 70 ml requires an intensive donation and significant loss of blood in the donation process. In a specific embodiment, cells from a small bone marrow donation (e.g., 7-10 ml) could be expanded by propagation in a placental bioreactor before infusion into a recipient.

In another embodiment, the embryonic-like stem cells can be used in a supplemental treatment in addition to chemotherapy. Most chemotherapy agents used to target and destroy cancer cells act by killing all proliferating cells, i.e., cells going through cell division. Since bone marrow is one of the most actively proliferating tissues in the body, hematopoietic stem cells are frequently damaged or destroyed by chemotherapy agents and in consequence, blood cell production is diminishes or ceases. Chemotherapy must be terminated at intervals to allow the patient's hematopoietic system to replenish the blood cell supply before resuming chemotherapy. It may take a month or more for the formerly quiescent stem cells to proliferate and increase the white blood cell count to acceptable levels so that chemotherapy may resume (when again, the bone marrow stem cells are destroyed).

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, embryonic-like stem cells or progenitor cells collected according to the methods of the invention could be introduced into the patient. Such treatment would reduce the time the patient would exhibit a low blood cell count, and would therefore permit earlier resumption of the chemotherapy treatment.

In another embodiment, the human placental stem cells can be used to treat or prevent genetic diseases such as chronic granulomatous disease.

5.6 Pharmaceutical Compositions

The present invention encompasses pharmaceutical compositions comprising a dose and/or doses effective upon single or multiple administration, prior to or following transplantation of conditioned or unconditioned human progenitor stem cells, exerting effect sufficient to inhibit, modulate and/or regulate the differentiation of human pluripotent and multipotent progenitor stem cells of placental origin into mesodermal and/or hematopoietic lineage cells.

In accordance with this embodiment, the embryonic-like stem cells of the invention may be formulated as an injectable (e.g., PCT WO 96/39101, incorporated herein by reference in its entirety). In an alternative embodiment, the cells and tissues of the present invention may be formulated using polymerizable or cross linking hydrogels as described in U.S. Pat. Nos. 5,709,854; 5,516,532; 5,654,381; each of which is incorporated by reference in their entirety.

6. EXAMPLE

6.1. Example 1

Analysis of Cell Types Recovered from Perfusate of Drained Placenta

This example describes the analysis of the cell types recovered from the effluent perfusate of a placenta cultured according to the methods of the invention.

Twenty ml of phosphate buffered saline solution (PBS) was added to the perfusion liquid and a 10 ml portion was collected and centrifuged for 25 minutes at 3000 rpm (revolutions per minute). The effluent was divided into four tubes and placed in an ice bath. 2.5 ml of a 1% fetal calf serum (FCS) solution in PBS was added and the tubes were centrifuged (140 minutes×10 g (acceleration due to gravity)). The pellet was resuspended in 5 ml of 1% FCS and two tubes were combined. The total mononucleocytes were calculated by adding the total lymphocytes and the total monocytes, and then multiplying the result by the total cell suspension volume.

The following table discloses the types of cells obtained by perfusion of a cultured placenta according to the methods described hereinabove.

| | WBC 1000/ml | Lym % | MID % | GRA % | Total Volume | # of Cells |
|---|---|---|---|---|---|---|
| CB (Cord Blood) | 10.5 | 43.2 | 8 | 48.8 | 60 ml | $6.3 \times 10^8$ |
| PP (Placenta perfusate, room temperature) | 12.0 | 62.9 | 18.2 | 18.9 | 15 ml | $1.8 \times 10^8$ |
| $PP_2$ (Placenta perfusate, 37° C.) | 11.7 | 56.0 | 19.2 | 24.8 | 30 ml | $3.5 \times 10^8$ |

Samples of PP were after Ficoll.
Total cell number of PP after Ficoll was $5.3 \times 10^8$ and number of CB before processing is $6.3 \times 10^8$.
Lym % indicates percent of lymphocytes;
MID % indicates percent of midrange white blood cells; and
GRA % indicates percent of granulocytes.

6.2. Example 2

Analysis of Cells Obtained by Perfusion and Incubation of Placenta

The following example describes an analysis of cells obtained by perfusion and incubation of placenta according to the methods of the invention.

6.2.1. Materials and Methods

Placenta donors were recruited from expectant mothers that enrolled in private umbilical cord blood banking programs and provided informed consent permitting the use of the exsanguinated placenta following recovery of cord blood for research purposes. Donor data may be confidential. These donors also permitted use of blinded data generated from the normal processing of their umbilical cord blood specimens for cryopreservation. This allowed comparison between the composition of the collected cord blood and the effluent perfusate recovered using the experimental method described below.

Following exsanguination of cord blood from the umbilical cord and placenta is stored at room temperature and delivered to the laboratory within four to twenty-four hour, according to the methods described hereinabove, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23±2° C.) or refrigerated (4° C.) in sterile containers for 2 to 20 hours. Periodically, the placentas were immersed and washed in sterile saline at 25±3° C. to remove any visible surface blood or debris.

The umbilical cord was transected approximately 5 cm from its insertion into the placenta and the umbilical vessels were cannulated with TEFLON® or polypropylene catheters connected to a sterile fluid path allowing bi-directional perfusion of the placenta and recovery of the effluent fluid. The methods described hereinabove enabled all aspects of placental conditioning, perfusion and effluent collection to be performed under controlled ambient atmospheric conditions as well as real-time monitoring of intravascular pressure and flow rates, core and perfusate temperatures and recovered effluent volumes. A range of conditioning protocols were evaluated over a 24-hour postpartum period, and the cellular composition of the effluent fluid was analyzed by flow cytometry, light microscopy and colony forming unit assays.

6.2.2. Placental Conditioning

The donor placentas were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection.

The donor placentas were maintained under varying conditions such as maintenance at 5-37° 5% $CO_2$, pH 7.2 to 7.5, preferably pH 7.45, in an attempt to simulate and sustain a physiologically compatible environment for the proliferation and recruitment of residual embryonic-like stem cells. The cannula was flushed with IMDM serum-free medium (GibcoBRL, NY) containing 2 U/ml heparin (Elkins-Sinn, NJ). Perfusion of the placenta continued at a rate of 50 ml per minute until approximately 150 ml of perfusate was collected. This volume of perfusate was labeled "early fraction." Continued perfusion of the placenta at the same rate resulted in the collection of a second fraction of approximately 150 ml and was labeled "late fraction." During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were then perfused with heparinized (2 U/ml) Dulbecco's modified Eagle Medium (H.DMEM) at the rate of 15 ml/minute for 10 minutes and the perfusates were collected from the maternal sites within one hour and the nucleated cells counted. The perfusion and collection procedures were repeated once or twice until the number of recovered nucleated cells fell below 100/ml. The perfusates were pooled and subjected to light centrifugation to remove platelets, debris and de-nucleated cell membranes. The nucleated cells were then isolated by Ficoll-Hypaque density gradient centrifugation and after washing, resuspended in H.DMEM. For isolation of the adherent cells, aliquots of $5$-$10 \times 10^6$ cells were placed in each of several T-75 flasks and cultured with commercially available Mesenchymal Stem Cell Growth Medium (MSCGM) obtained from BioWhittaker, and placed in a tissue culture incubator (37° C., 5% $CO_2$). After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

6.2.3. Cell Recovery and Isolation

Cells were recovered from the perfusates by centrifugation at 5000×g for 15 minutes at room temperature. This procedure served to separate cells from contaminating debris and platelets. The cell pellets were resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by "differential trypsinization," using a solution of 0.05% trypsin with 0.2% EDTA (Sigma, St. Louis Mo.). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization, using Trypsin Neutralizing Solution (TNS, BioWhittaker). The cells were washed in H.DMEM and resuspended in MSCGM.

Flow cytometry was carried out using a Becton-Dickinson FACSCalibur instrument and FITC and PE labeled monoclonal antibodies (mAbs), selected on the basis of known markers for bone marrow-derived MSC (mesenchymal stem cells), were purchased from B.D. and Caltag laboratories (South San Francisco, Calif.), and SH2, SH3 and SH4 antibody producing hybridomas were obtained from and reactivities of the mAbs in their cultured supernatants were detected by FITC or PE labeled F(ab)'2 goat anti-mouse antibodies. Lineage differentiation was carried out using commercially available induction and maintenance culture media (BioWhittaker), used as per manufacturer's instructions.

6.2.4. Isolation of Placental Embryonic-Like Stem Cells

Microscopic examination of the adherent cells in the culture flasks revealed morphologically different cell types. Spindle-shaped cells, round cells with large nuclei and numerous perinuclear small vacuoles, and star-shaped cells with several projections (through one of which star-shaped cells were attached to the flask) were observed adhering to the culture flasks. Although no attempts were made to further characterize these adherent cells, similar cells were observed in the culture of bone marrow, cord and peripheral blood, and therefore considered to be non-stem cell-like in nature. The fibroblastoid cells, appearing last as clusters, were candidates for being MSC (mesenchymal stem cells) and were isolated by differential trypsinization and subcultured in secondary flasks. Phase microscopy of the rounded cells, after trypsinization, revealed that the cells were highly granulated; indistinguishable from the bone marrow-derived MSC produced in the laboratory or purchased from BioWhittaker. When subcultured, the placenta-derived embryonic-like stem cells, in contrast to their earlier phase, adhered within hours, assumed characteristic fibroblastoid shape, and formed a growth pattern identical to the reference bone marrow-derived MSC. During subculturing and refeeding, moreover, the loosely bound mononuclear cells were washed out and the cultures remained homogeneous and devoid of any visible non-fibroblastoid cell contaminants.

6.2.5. Results

The expression of CD-34, CD-38, and other stem cell-associated surface markers on early and late fraction purified mononuclear cells was assessed by flow cytometry. Recovered, sorted cells were washed in PBS and then double-stained with antiCD34 phycoerythrin and anti-CD38 fluorescein isothiocyanate (Becton Dickinson, Mountain View, Calif.).

Cell isolation was achieved by using magnetic cell separation, such as for example, Auto Macs (Miltenyi). Preferably, CD 34+ cell isolation is performed first.

6.3 Example 3

Perfusion Medium

The following example provides a formula of the preferred perfusate solution for the cultivation of isolated placentas

| Chemical | Source | Stock Concentration | Final Concentration | 500 ml |
|---|---|---|---|---|
| DMEM-LG | GibcoBRL11885-084 | | | 300 ml |
| MCDB201 | Sigma M-6770 | dissolved in H2O | pH to 7.2. filter | 200 ml |
| FCS | Hyclone | 100% | 2% | 10 ml |
| ITS | Sigma I-3146 or GibcoBRL41400-045 | 100x | 1x | 5 ml |
| Pen&Strep | GibcoBRL15140-122 | 100x | 1x | 5 ml |
| LA + BSA | Sigma + GibcoBRL BSA | 100x(1 μg/ml of LA | 10 ng/ml of LA | 5 ml |
| Dexamethasone | Sigma D-2915 | 0.25 mM in H2O | 0.05 μM | 100 μl |
| L-Ascorbic Acid | Sigma A-8960 | 1000x(100 mM) | 1x(0.1 mM) | 500 μl |
| PDGF (50 μg) | R&D 220BD | 10 μg/ml in 4 mM HCl + 0.1% BSA | 10 ng/ml | 500 μl |
| EGF (200 μg) | Sigma E-9644 | 10 μg/ml in 10 mM HAc + 0.1% BSA | 10 ng/ml | 500 μl |

The above-composition is a perfusate that may be used at a variety of temperatures to perfuse placenta. It should be noted that additional components such as antibiotics, anticoagulant and other growth factors may be used in the perfusate or culture media.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method of repairing heart tissue in an individual that has suffered from myocardial infarction, comprising administering to the individual a therapeutically effective amount of isolated human placental stem cells, wherein said placental stem cells are:

OCT-4+, CD34−, CD10+, CD29+, CD44+, CD45−, CD54+, CD90+, SH3+, SH4+, SSEA3−, and/or SSEA4−, wherein OCT-4 is octamer binding protein 4;

OCT-4$^+$, CD34$^-$, SSEA3$^-$ and SSEA4$^-$;

OCT-4$^+$ and CD34$^-$, and additionally SH3$^+$ or SH4$^+$; or

CD34$^-$ and one or more of CD29$^+$, CD45$^-$, CD90$^+$, SH2$^+$, SH3$^+$, SH4$^+$, or MHC Class II$^-$.

2. The method of claim 1, wherein said placental stem cells are OCT-4$^+$, CD34$^-$, CD10$^+$, CD29$^+$, CD44$^+$, CD45$^-$, CD54$^+$, CD90$^+$, SH3$^+$, SH4$^+$, SSEA3$^-$, and SSEA4$^-$.

3. The method of claim 1, wherein said placental stem cells are OCT-4$^+$, CD34$^-$, SSEA3$^-$ and SSEA4$^-$.

4. The method of claim 3, wherein said placental stem cells are additionally SH3$^+$ or SH4$^+$.

5. The method of claim 3, wherein said placental stem cells are additionally SH3$^+$ and SH4$^+$.

6. The method of claim 3, wherein said placental stem cells are additionally CD29$^+$, CD45$^-$, CD90$^+$, SH2$^+$, SH3$^+$, SH4$^+$, or MHC Class II$^-$.

7. The method of claim 3, wherein said placental stem cells have at least one of the following additional characteristics: CD10$^+$, CD29$^+$, CD44$^+$, CD45$^-$, CD54$^+$, CD90$^+$, SSEA3$^-$, or SSEA4$^-$.

8. The method of claim 3, wherein said placental stem cells have at least the following additional characteristics: CD10$^+$, CD29$^+$, CD44$^+$, CD45$^-$, CD54$^+$, CD90$^+$, SSEA3$^-$, and SSEA4$^-$.

9. The method of claim 3, wherein said placental stem cells have at least one of the following additional characteristics: CD10$^+$, CD29$^+$, CD44$^+$, CD45$^-$, CD54$^+$, or CD90$^+$.

10. The method of claim 3, wherein said placental stem cells have at least the following additional characteristics: CD10$^+$, CD29$^+$, CD44$^+$, CD45$^-$, CD54$^+$, and CD90$^+$.

* * * * *